US012036269B2

(12) United States Patent
Georgiou et al.

(10) Patent No.: US 12,036,269 B2
(45) Date of Patent: Jul. 16, 2024

(54) HUMAN-ENZYME MEDIATED DEPLETION OF HOMOCYSTEINE FOR TREATING PATIENTS WITH HYPERHOMOCYSTEINEMIA AND HOMOCYSTINURIA

(71) Applicant: Board of Regents, The University of Texas System, Austin, TX (US)

(72) Inventors: George Georgiou, Austin, TX (US); Everett Stone, Austin, TX (US); Wei-Cheng Lu, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/330,106

(22) Filed: May 25, 2021

(65) Prior Publication Data
US 2021/0386838 A1 Dec. 16, 2021

Related U.S. Application Data

(62) Division of application No. 15/977,299, filed on May 11, 2018, now Pat. No. 11,033,612.

(60) Provisional application No. 62/505,493, filed on May 12, 2017.

(51) Int. Cl.
| | | |
|---|---|---|
| C12N 9/96 | (2006.01) | |
| A61K 9/00 | (2006.01) | |
| A61K 9/19 | (2006.01) | |
| A61K 38/51 | (2006.01) | |
| A61K 47/60 | (2017.01) | |
| A61P 7/00 | (2006.01) | |
| C12N 9/88 | (2006.01) | |
| C12N 15/70 | (2006.01) | |
| C12N 15/80 | (2006.01) | |
| C12N 15/861 | (2006.01) | |
| C12N 15/867 | (2006.01) | |
| C12N 15/869 | (2006.01) | |
| A61K 31/198 | (2006.01) | |
| A61K 31/4415 | (2006.01) | |

(52) U.S. Cl.
CPC ............ *A61K 38/51* (2013.01); *A61K 9/0019* (2013.01); *A61K 9/19* (2013.01); *A61K 47/60* (2017.08); *A61P 7/00* (2018.01); *C12N 9/88* (2013.01); *C12N 9/96* (2013.01); *C12N 15/70* (2013.01); *C12N 15/80* (2013.01); *C12N 15/861* (2013.01); *C12N 15/867* (2013.01); *C12N 15/869* (2013.01); *C12Y 404/01001* (2013.01); *A61K 31/198* (2013.01); *A61K 31/4415* (2013.01)

(58) Field of Classification Search
CPC . C12N 9/88; C12N 9/96; C12N 15/70; C12N 15/80; C12N 15/861; C12N 15/867; C12N 15/869; C12Y 404/01001
See application file for complete search history.

(56) References Cited

U.S. PATENT DOCUMENTS

| | | |
|---|---|---|
| 4,870,287 A | 9/1989 | Cole et al. |
| 5,739,169 A | 4/1998 | Ocain et al. |
| 5,760,395 A | 6/1998 | Johnstone |
| 5,824,311 A | 10/1998 | Greene et al. |
| 5,830,880 A | 11/1998 | Sedlacek et al. |
| 5,846,945 A | 12/1998 | McCormick |
| 5,889,155 A | 3/1999 | Ashkenazi et al. |
| 8,709,407 B2 | 4/2014 | Georgiou et al. |
| 9,279,119 B2 | 3/2016 | Georgiou et al. |
| 9,481,877 B2 | 11/2016 | Georgiou et al. |
| 9,624,484 B2 | 4/2017 | Georgiou et al. |
| 9,909,163 B2 | 3/2018 | Georgiou et al. |
| 10,233,438 B2 | 3/2019 | Georgiou et al. |
| 2005/0036981 A1 | 2/2005 | Yagi et al. |
| 2005/0036984 A1 | 2/2005 | Harrison et al. |
| 2006/0107342 A1 | 5/2006 | Amir |
| 2006/0275279 A1 | 12/2006 | Rozzell et al. |
| 2009/0304666 A1 | 12/2009 | Harrison et al. |
| 2011/0200576 A1 | 8/2011 | Georgiou et al. |
| 2012/0156672 A1 | 6/2012 | Otte et al. |
| 2014/0287484 A1 | 9/2014 | Georgiou et al. |
| 2015/0064159 A1 | 3/2015 | Georgiou et al. |
| 2015/0064160 A1 | 3/2015 | Georgiou et al. |
| 2018/0002685 A1 | 1/2018 | Georgiou et al. |
| 2018/0008681 A1 | 1/2018 | Stone |

(Continued)

FOREIGN PATENT DOCUMENTS

| | | |
|---|---|---|
| CN | 102791856 A | 11/2012 |
| CN | 105531371 A | 4/2016 |
| CN | 105612252 A | 5/2016 |

(Continued)

OTHER PUBLICATIONS

Dang, A Q, and D E Cook. "The transsulfuration pathway in Tetrahymena pyriformis." *Biochimica et biophysica acta* vol. 496,2 (1977): 264-71.

(Continued)

*Primary Examiner* — Iqbal H Chowdhury
(74) *Attorney, Agent, or Firm* — Parker Highlander PLLC

(57) ABSTRACT

Methods and compositions relating to the engineering of an improved protein with homocyst(e)inase enzyme activity are described. For example, there are disclosed modified cystathionine-γ-lyase (CGL) enzymes comprising one or more amino acid substitutions and capable of degrading homocyst(e)ine. Furthermore, provided are compositions and methods for the treatment of homocystinuria or hyperhomocysteinemia with homocyst(e)ine depletion using the disclosed enzymes or nucleic acids.

16 Claims, 4 Drawing Sheets
Specification includes a Sequence Listing.

(56) References Cited

U.S. PATENT DOCUMENTS

2018/0171380 A1 6/2018 Georgiou et al.

FOREIGN PATENT DOCUMENTS

| JP | 2007-500696 | 1/2007 |
|---|---|---|
| JP | 2013-518594 | 5/2013 |
| JP | 2016-506727 | 3/2016 |
| JP | 2016-528917 | 9/2016 |
| KR | 10-2016-0045096 | 4/2016 |
| WO | WO 2002/020807 | 3/2002 |
| WO | WO 2011/097381 | 8/2011 |
| WO | WO 2014/120770 | 8/2014 |
| WO | WO 2015/031726 | 3/2015 |
| WO | WO 2015/031735 | 3/2015 |
| WO | WO 2018/009663 | 1/2018 |

OTHER PUBLICATIONS

Office Communication issued in Chinese Patent Application No. 2018800290829, dated Sep. 9, 2022. English Translation.
Office Communication issued in Japanese Patent Application No. 2019-562275, dated Feb. 24, 2022. English Translation.
"cystathionine gamma-lyase [Rattus norvegicus]" Genbank ID No. BAB19922.2, Apr. 20, 2001.
"cystathionine gamma-lyase homolog [imported]—Stenotrophomonas maltophilia" Genbank ID No. T45483, Jan. 31, 2000.
"Google Search—wei-cheng lu evolved enzymes for cancer therapeutics and orthogonal system," dated Jan. 18, 2017.
"Human recombinant Fc fused protein," Funakoshi News, Mar. 1, 2013. (Machine translation of Japanese text).
"hypothetical protein [Pongo abelii]" Genbank ID No. CAH89476. 1, May 1, 2008.
"Macaca fascicularis" Genbank ID No. AAW71993, Jan. 7, 2005.
"Pan troglodytes" Genbank ID No. XP_513486, May 13, 2011.
"Pongo abelii cystathionase (cystathionine gamma-lyase) (CTH), mRNA," Database DDBJ/EMBL/GeneBank [online], Accession No. NM_001131163, available at: http://www.ncbi.nlm.nih.gov/nuccore/197098155?sat-13&satkey=11125499, dated Aug. 20, 2008.
"Pongo abelii" Genbank ID No. NP_001124635, Mar. 10, 2011.
"probable cystathionine gamma-lyase PA0400 [imported]—Pseudomonas aeruginosa" Genbank ID No. F83595, Sep. 15, 2000.
Antikainen et al., "Altering protein specificity: techniques and applications," *Bioorganic & Medicinal Chemistry*, 13:2701-2716, 2005.
Ashe et al., "N5-methyltetrahydrofolate: homocysteine methyltransferase activity in extracts from normal, malignant and embryonic tissue culture cells," *Biochem. Biophys. Res. Commun.*, 57:417-425, 1974.
Breillout et al., In: *Methionine dependency of malignant tumors: a possible approach for therapy*, Oxford University Press, 1628-1632, 1990.
Breitinger et al., "The three-dimensional structure of cystathionine ß-lyase from *Arabidopsis* and its substrate specificity," *Plant Physiology*, 126:631-642, 2001.
Chica et al., "Semi-rational approaches to engineering enzyme activity: combining the benefits of directed evolution and rational design," *Curr Opin Biotechnol*, 16(4):378-84, 2005.
Cramer et al., "Systemic depletion of L-cyst(e)ine with cyst(e)inase increases reactive oxygen species and suppresses tumor growth," *Nat. Med.*, 21:120-127, 2016.
Doxsee et al., "Sulfasalazine-induced cystine starvation: Potential use for prostate cancer therapy," *The Prostate*, 67:162-171, 2007.
Ercolani et al., "Bladder outlet obstruction in male cystinuria mice," *Int. Urol. Nephrol.*, 42:57-63, 2010.
Esaki and Soda, "L-methionine gamma-lyase from *Pseudomonas putida* and *Aeromonas*," *Methods Enzymol.*, 143:459-465, 1987.
Extended European Search Report issued in European Application No. 14 84 1106, dated Jan. 30, 2017.
Feliubadalo et al., "Slc7a9-deficient mice develop cystinuria non-I and cystine urolithiasis," *Hum. Mol. Genet.*, 12:2097-2108, 2003.

Glode et al., "Cysteine auxotrophy of human leukemic lymphoblasts is associated with decreased amounts of intracellular cystathionase protein," *Biochemistry*, 20(5):1306-1311, 1981.
Goyer et al. "Functional Characterization of a Methionine gamma-Lyase in *Arabidopsis* and its Implication in an Alternative to the Reverse Trans-sulfuration Pathway," *Plant Cell Physiol.*, 48(2):232-242 (2007).
Guan et al., "The x c- cystine/glutamate antiporter as a potential therapeutic target for small-cell lung cancer: use of sulfasalazine," *Cancer Chemotherapy & Pharmacology*, 64(3):463-472, 2009.
Halpern et al., "The effect of replacement of methionine by homocystine on survival of malignant and normal adult mammalian cells in culture," *Proc. Natl. Acad. Sci. USA*, 71:1133-1136, 1974.
Hori et al., "Gene cloning and characterization of Pseudomonas putida L-methionine-alpha- deamino-gamma-mercaptomethane-lyase," *Cancer Res.*, 56:2116-2122, 1996.
Huang et al., "Site-directed mutagenesis on human cystathionine-gamma-lyase reveals insights into the modulation of H2S production," *Journal of Molecular Biology*, 396(3):708-718, 2009.
International Search Report and Written Opinion issued in International Application No. PCT/US2017/040897, dated Oct. 10, 2017.
International Search Report and Written Opinion issued in International Application No. PCT/US2014/053359, dated Mar. 23, 2015.
International Search Report and Written Opinion issued in International Application No. PCT/US2014/053374, dated Jan. 14, 2015.
International Search Report and Written Opinion issued in International Application No. PCT/US2018/032286, dated Jul. 6, 2018.
International Search Report and Written Opinion issued in International Application No. PCT/US2018/032246, dated Aug. 1, 2018.
Invitation to Pay Additional Fees issued in International Application No. PCT/US2014/053359, dated Jan. 16, 2015.
Ito et al., "Purification and characterization of methioninase from *Pseudomonas putida*," *J. Biochem.*, 79:1263-1272, 1976.
Khersonsky et al., "Enzyme promiscuity: evolutionary and mechanistic aspects," *Current Opinion in Chemical Biology*, 10:498-508, 2006.
Kim et al., "Expression of cystathionine ß-synthase is downregulated in hepatocellular carcinoma and associated with poor prognosis," *Oncology Reports*, 21(6):1449-1454, 2009.
Knoll, Thomas, et al. "Cystinuria in childhood and adolescence: recommendations for diagnosis, treatment, and follow-up." *Pediatric Nephrology* 20.1 (2005): 19-24.
Kraus et al., "Cystathionine γ-lyase: clinical, metabolic, genetic, and structural studies," *Mol. Genet. Metab.*, 97:250-259, 2009.
Kreis and Goodenow, "Methionine requirement and replacement by homocysteine in tissue cultures of selected rodent and human malignant and normal cells," *Cancer Res.*, 38:2259-2262, 1978.
Kreis et al., "Effect of nutritional and enzymatic methionine deprivation upon human normal and malignant cells in tissue culture," *Cancer Res.*, 40:634-641, 1980.
Kreis, "Tumor therapy by deprivation of L-methionine: rationale and results," *Cancer Treatment Rpts.*, 63:1069-1072, 1979.
Kudou et al., "Structure of the antitumour enzyme L-methionine gamma-lyase from Pseudomonas putida at 1.8 A resolution," *J. Biochem.*, 141:535-544, 2007.
Link et al., "Cystathionase: a potential cytoplasmic marker of hematopoietic differentiation," *Blut*, 47(1):31-39, 1983.
Lishko et al., "Depletion of serum methionine by methioninase in mice," *Anticancer Res.*, 13:1465-1468, 1993.
Liu et al., "Methionine dependency and the therapy of tumor," *Parenteral and Enteral Nutrition*, 12(4):247-250, 2005. (English Abstract).
Livrozet et al., "An animal model of Type A Cystinuria due to spontaneous mutation in 129S2/SvPasCrl Mice," *PLoS ONE*, 9:e102700, 2014.
Lu et al., "Cloning and nucleotide sequence of human liver cDNA encoding for cystathionine gamma-lyase," *Biochem. Biophys. Res. Commun.*, 189:749-758, 1992 (Abstract only).
Lu, "Evolved enzymes for cancer therapeutics and orthogonal system," *Dissertation—The University of Texas at Austin*, Aug. 2013.
Messerschmidt et al., "Determinants of enzymatic specificity in the Cys-Met-metabolism PLP-dependent enzymes family: crystal struc-

(56) References Cited

OTHER PUBLICATIONS ture of cystathionine gamma-lyase from yeast and intrafamiliar structure comparison," *Biol. Chem.*, 384:373-386, 2003.
Motoshima et al., "Crystal structure of the pyridoxal 5'-phospate dependent L-methionine gamma-lyase from Pseudomaonas putida," *J. Biochem.*, 128(3):349-354, 2000.
Mudd et al., "Homocystinuria: an enzymatic defect," *Science*, 143:1443-1445, 1964.
Nakayama et al., "Purification of bacterial L-methionine gamma-lyase," *Anal. Biochem.*, 138:421-424, 1984.
Nygård et al., "Major lifestyle determinants of plasma total homocysteine distribution: the Hordaland Homocysteine Study," *The American Journal of Clinical Nutrition*, 67:263-270, 1998.
Office Communication issued in Australian Patent Application No. 2011212885, dated Oct. 27, 2014.
Office Communication issued in Australian Patent Application No. 2014312159, dated Aug. 10, 2018.
Office Communication issued in Canadian Patent Application No. 2,788,689, dated Dec. 27, 2017.
Office Communication issued in Chinese Patent Application No. 201180013307, dated Apr. 9, 2014.
Office Communication issued in Chinese Patent Application No. 201180013307, dated Mar. 29, 2013.
Office Communication issued in Chinese Patent Application No. 201180013307, dated Oct. 25, 2013.
Office Communication issued in European Patent Application No. 14839001.6, dated Feb. 17, 2017.
Office Communication issued in European Patent Application No. 14839001.6, dated Mar. 5, 2018.
Office Communication issued in Israeli Patent Application No. 244263, dated Sep. 16, 2018.
Office Communication issued in Japanese Patent Application No. 2012-552084, dated Aug. 24, 2015. (English translation of Japanese text).
Office Communication issued in Japanese Patent Application No. 2012-552084, dated Mar. 12, 2015. (English translation of Japanese text).
Office Communication issued in Japanese Patent Application No. 2016-537882, dated Aug. 9, 2018.
Office Communication issued in Japanese Patent Application No. 2016-537886, dated Jun. 20, 2018.
Office Communication issued in U.S. Appl. No. 13/020,268, dated Dec. 11, 2012.
Office Communication issued in U.S. Appl. No. 13/020,268, dated Jun. 18, 2013.
Office Communication issued in U.S. Appl. No. 14/472,779, dated Jun. 2, 2015.
Office Communication issued in U.S. Appl. No. 14/472,779, dated Oct. 28, 2015.
Office Communication issued in U.S. Appl. No. 14/472,750, dated Dec. 31, 2015.
Office Communication issued in U.S. Appl. No. 15/052,978, dated Jul. 6, 2017.
Office Communication issued in U.S. Appl. No. 15/451,349, dated Jul. 16, 2018.
PCT International Search Report and Written Opinion, issued in International Application No. PCT/US2011/023606, dated Oct. 25, 2011.
Paley, Olga M. *Engineering a novel human methionine degrading enzyme as a broadly effective cancer therapeutic. Dissertation—The University of Texas at Austin*, Aug. 2014.
Peters et al., "A mouse model for cystinuria type I," *Hum. Mol. Genet.*, 12:2109-2120, 2003.
Rao et al., "Role of the transsulfuration pathway and of gamma-cystathionase activity in the formation of cysteine and sulfate from methionine in rat hepatocytes," *J. Nutrition*, 120:837-845, 1990.
Response to Office Communication issued in Chinese Patent Application No. 201180013307, dated Jul. 29, 2013.
Response to Office Communication issued in Chinese Patent Application No. 201180013307, dated Dec. 5, 2013.
Response to Office Communication issued in U.S. Appl. No. 13/020,268, dated Oct. 9, 2013.
Sato and Nozaki, "Methionine gamma-lyase: the unique reaction mechanism, physiological roles, and therapeutic applications against infectious diseases and cancers," *IUMBM Life*, 61:1019-1028, 2009.
Schellenberger et al., "A recombinant polypeptide extends the in vivo half-life of peptides and proteins in a tunable manner," *Nat. Biotechnol.*, 27:1186-1190, 2009.
Sridhar et al., "Crystallization and preliminary crystallographic characterization of recombinant L-methionine-alpha-deamino-gamma-mercaptomethane lyase (methioninase)," *Acta. Crystall. Section D Biol. Crystall.*, 56:1665-1667, 2000.
Steegborn et al., "Kinetics and inhibition of recombinant human cystathionine gamma-lyase. Toward the rational control of transsulfuration," *J. Biol. Chem.*, 274:12675-12684, 1999.
Stone et al., "De novo engineering of a human cystathionine-γ-lyase for systemic (L)-Methionine depletion cancer therapy," *ACS Chem. Biol.*, 7(11):1822-1829, 2012.
Stone et al., "De novo engineering of a human cystathionine-γ-lyase for systemic (L)-Methionine depletion cancer therapy," *ACS Chem. Biol.*, 7(11):1822-1829, 2012. Supporting Information.
Stone et al., "Strategies for optimizing the serum persistence of engineered human arginase I for cancer therapy," *Journal of Controlled Release*, 158:171-179, 2012.
Sun et al., "In vivo efficacy of recombinant methioninase is enhanced by the combination of polyethylene glycol conjugation and pyridoxal 5'-phosphate supplementation," *Cancer Research*, 63:8377-8383, 2003.
Takakura et al., "Assay method for antitumor L-methionine -lyase: comprehensive kinetic analysis of the complex reaction with L-methionine." *Analytical Biochemistry*, 327(2):233-240, 2004.
Tan et al., "Anticancer efficacy of methioninase in vivo," *Anticancer Res.*, 16:3931-3936, 1996.
Tan et al., "Overexpression and large-scale production of recombinant L-methionine-alpha-deamino-gamma-mercaptomethane-lyase for novel anticancer therapy," *Protein Expr. Purif.*, 9:233-245, 1997.
Tan et al., "Recombinant methioninase infusion reduces the biochemical endpoint of serum methionine with minimal toxicity in high-stage cancer patients," *Anticancer Res.*, 17:3857-3860, 1997.
Tan et al., "Serum methionine depletion without side effects by methioninase in metastatic breast cancer patients," *Anticancer Res.*, 16:3937-3942, 1996.
Tiziani et al., "Metabolomics of the tumor microenvironment in pediatric acute lymphoblastic leukemia," *PLoS ONE*, 8:e82859, 2013.
Tiziani et al., "Optimized metabolite extraction from blood serum for 1H nuclear magnetic resonance spectroscopy," *Analytical Biochemistry*, 377:16-23, 2008.
Walter et al., "Strategies for the treatment of cystathionine beta-synthase deficiency: the experience of the Willink Biochemical Genetics Unit over the past 30 years," *European Journal of Pediatrics*, 157:S71-S76, 1998.
Wawrzynczak and Thorpe, In: *Immunoconjugates, Antibody Conjugates In Radioimaging and Therapy of Cancer*, Vogel (Ed.), NY, Oxford University Press, pp. 28-55, 1987.
Whisstock et al., "Prediction of protein function from protein sequence and structure," *Quarterly Reviews of Biophysics*, 36(3): 307-40, 2003.
Witkowski et al., "Conversion of a ß-Ketoacyl Synthase to a Malonyl Decarboxylase by Replacement of the Active-Site Cysteine with Glutamine," *Biochemistry*, 38(36): 11643- 11650, 1999.
Yan et al., "Structural Snapshots of an Engineered Cystathionine-[gamma]-lyase Reveal the Critical Role of Electrostatic Interactions in the Active Site," *Biochemistry*, 56(6):876-885, 2017.
Yang et al., "PEGylation confers greatly extended half-life and attenuated immunogenicity to recombinant methioninase in primates," *Cancer Research*, 64:6673-6678, 2004.
Yang et al., "Pharmacokinetics, methionine depletion, and antigenicity of recombinant methioninase in primates," *Clinical Cancer Research*, 10:2131-2138, 2004.
Yoshioka et al., "Anticancer efficacy in vivo and in vitro, synergy with 5-fluorouracil, and safety of recombinant methioninase," *Cancer Res.*, 58:2583-2587, 1998.

(56) References Cited

OTHER PUBLICATIONS

Zhang et al., "Stromal control of cysteine metabolism promotes cancer cell survival in chronic lymphocytic leukemia," *Nat. Cell Biol.*, 14:276-286, 2012.

Zhao et al., "Frequent Epigenetic Silencing of the Folate-Metabolising Gene Cystathionine-Beta-Synthase in Gastrointestinal Cancer," *PLoS ONE*, 7(11):e49683, 2012.

Zhu et al., "Kinetic properties of polymorphic variants and pathogenic mutants in human cystathionine γ-lyase," *Biochemistry*, 47:6226-6232, 2008.

Ishii, Isao et al. "Cystathionine gamma-Lyase-deficient mice require dietary cysteine to protect against acute lethal myopathy and oxidative injury." *The Journal of biological chemistry* vol. 285,34 (2010): 26358-68.

Office Communication issued in Korean Patent Application No. 10-2019-7036481, dated May 12, 2023. English Translation.

FIG. 6

HUMAN-ENZYME MEDIATED DEPLETION OF HOMOCYSTEINE FOR TREATING PATIENTS WITH HYPERHOMOCYSTEINEMIA AND HOMOCYSTINURIA

REFERENCE TO RELATED APPLICATIONS

The present application is a divisional of U.S. patent application Ser. No. 15/977,299, filed May 11, 2018, which claims the priority benefit of U.S. provisional application No. 62/505,493, filed May 12, 2017, the entire contents of each of which is incorporated herein by reference.

STATEMENT REGARDING FEDERALLY SPONSORED RESEARCH

This invention was made with government support under Grant No. RO1 CA139059 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on May 24, 2021, is named UTSBP1138USD1 ST25.txt and is 230 kilobytes in size.

BACKGROUND

1. Field

Disclosed are recombinantly engineered primate enzyme variants having homocysteine degrading activity and stability suitable for use in human therapy. Compositions and methods for the treatment of homocystinuria and hyperhomocysteinemia with enzymes that degrade homocysteine and homocystine are also provided.

2. Description of Related Art

Homocystinuria a rare disease resulting from an inborn error of metabolism involving sulfur amino acids. Classical homocystinuria, the most common form, is caused by defects in the cystathionine β-synthase (CBS) enzyme (Mudd et al., 1964) while nonclassical homocystinuria is commonly associated with defects in various enzymes (e.g., MTHFR, MTRR, or MTR) involved in folate metabolism (Kang et al., 1987). Patients with homocystinuria often display thromboembolisms, cognitive impairment, osteoporosis, and ocular lens dislocation (Kruger et al., 2003). Patients also suffer from hyperhomocysteinemia, a condition in which serum homocysteine (Hcy) concentrations exceed 15 µM. Patients with classical homocystinuria, as well as a few nonclassical forms, often display elevated levels of serum methionine (Met), while having depleted levels of cystathionine (Cth) and cysteine (Cys) (Kruger et al., 2003). It has been estimated to impact up to 1 in 344,000 people worldwide, however, its prevalence is significantly higher in some countries. The most common medical conditions associated with classical homocystinuria are cardiovascular complications including an increased risk of blood clots. Other symptoms include skeletal abnormalities, dislocation of the lens in the eye, and development and learning defects.

Currently available treatments for classical homocystinuria include methionine-restricted diets as well as high doses of vitamin B6 and betaine (N,N,N-trimethylglycine), the latter reducing homocysteine levels. These treatments focus on preventing the buildup of Hcy and show moderate to limited efficacy (Walter et al., 1998). Although these treatments can be effective for some patients, responses fluctuate significantly due to the variations in the genetic mutation driving the disease. As a result, there exists an opportunity to develop a therapy that addresses the need of all patients by reducing blood homocystine levels back to the normal range. Therefore, new methods and compositions for treating these patients are needed.

SUMMARY

Methods are disclosed of utilizing an engineered human cystathionine-gamma-lyase (CGL) enzyme that efficiently degrades homocyst(e)ine, such that it is a suitable therapy for treating homocystinuria and hyperhomocysteinemia patients by degrading excess serum homocyst(e)ine and providing a sink for intracellular homocyst(e)ine. The method may reduce the serum homocysteine level (tHcy) to a level of less than 25 µM.

Methods of treatment comprising administering a modified CGL enzyme, a nucleic acid encoding a modified CGL enzyme in a gene therapy vector, or a formulation comprising the modified CGL enzyme, and in particular methods of treating subjects with homocystinuria or hyperhomocysteinemia, are provided. The subject may be any animal, such as a mouse. For example, the subject may be a mammal, a rodent, a primate, or a human patient. The method may comprise selecting a patient with homocystinuria or hyperhomocysteinemia. The subject or patient may be maintained on a methionine-restricted diet or a normal diet in combination with being treated with the described compositions.

Provided herein are human cystathionine-γ-lyase (hCGL) mutants with catalytic activity toward homocyst(e)ine for use in the method of treatment. For example, the enzyme variant may have an amino acid sequence selected from the group consisting of SEQ ID NOs: 2-6 and 37-39. In particular, the variant may be derived from human enzymes, such as human cystathionine-γ-lyase (CGL). Polypeptides are provided comprising a modified human CGL capable of degrading homocyst(e)ine. The polypeptide may be capable of degrading homocyst(e)ine under physiological conditions. For example, the polypeptide may display a catalytic activity towards L-homocystine up to $k_{cat}/K_M$ of 100, 95, 90, 85, 80, 75, 70, 65, 60, 55, 50, 45, 40, 35, 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, 0.01, 0.005, 0.001 $mM^{-1}s^{-1}$ or any range derivable therein.

These enzymes were engineered by introducing amino acid substitutions in the human enzyme cystathionine-γ-lyase (CGL). The variants having amino acid substitutions include SEQ ID NO: 2, hCGL-E59N-R119L-E339V (hCGL-NLV); SEQ ID NO: 3, hCGL-E59N-S63L-L91M-R119L-K268R-T311G-E339V-I353S (hCGL-Smut-1); SEQ ID NO: 4, hCGL-E59I-S63L-L91M-R119L-K268R-T311G-E339V-I353S (hCGL-Smut-2); SEQ ID NO: 5, hCGL-E59N-S63L-L91M-R119A-K268R-T311G-E339V-I353S (hCGL-Smut-3); SEQ ID NO: 6, hCGL-E59I-S63L-L91M-R119A-K268R-T311G-E339V-I353S (hCGL-Smut-4); SEQ ID NO: 27, hCGL-E59N-R119L-T336D-E339V (hCGL-NLDV); SEQ ID NO: 28, hCGL-E59N-S63L-L91M-R119L-K268R-T311G-T336D-E339V-I353S (hCGL-9mutD-1); SEQ ID NO: 29, hCGL-E59I-S63L-

L91M-R119L-K268R-T311G-T336D-E339V-I353S (hCGL-9mutD-2); SEQ ID NO: 30, hCGL-E59N-563L-L91M-R119A-K268R-T311G-T336D-E339V-I353S (hCGL-9mutD-3); SEQ ID NO: 31, hCGL-E59I-563L-L91M-R119A-K268R-T311G-T336D-E339V-I353S (hCGL-9mutD-4); SEQ ID NO: 32, hCGL-E59N-R119L-T336E-E339V (hCGL-NLEV); SEQ ID NO: 33, hCGL-E59N-563L-L91M-R119L-K268R-T311G-T336E-E339V-I353S (hCGL-9mutE-1); SEQ ID NO: 34, hCGL-E59I-563L-L91M-R119L-K268R-T311G-T336E-E339V-I353S (hCGL-9mutE-2); SEQ ID NO: 35, hCGL-E59N-563L-L91M-R119A-K268R-T311G-T336E-E339V-I353S (hCGL-9mutE-3); SEQ ID NO: 36, hCGL-E59I-563L-L91M-R119A-K268R-T311G-T336E-E339V-I353S (hCGL-9mutE-4); SEQ ID NO: 37, hCGL-E59I-563L-L91M-R119D-K268R-T311G-E339V-I353S (Mutant 3); SEQ ID NO: 38, hCGL-E59I-563L-L91M-R119H-K268R-T311G-E339V-I353S (Mutant 4); and SEQ ID NO: 39, hCGL-E59I-563L-L91M-R119G-K268R-T311G-E339V-I353S (Mutant 5).

A modified CGL enzyme as discussed herein may be characterized as having a certain percentage of identity as compared to an unmodified CGL enzyme (e.g., a native CGL enzyme). For example, the unmodified CGL enzyme may be a native primate cystathionase (i.e., cystathionine-γ-lyase). The percentage identity may be at least 90%, 95%, 96%, 97%, 98%, 99% or 100% (or any range derivable therein) between the unmodified portions of a modified CGL enzyme (i.e., the sequence of the modified CGL enzyme excluding any substitutions at amino acid positions 59, 63, 91, 119, 268, 311, 336, 339 and/or 353 of SEQ ID NO: 1 and its cognate positions in SEQ ID NOS: 7-10, see FIG. 6) and the native CGL enzyme. It is also contemplated that the percent identity discussed above may relate to a particular modified region of an enzyme as compared to an unmodified region of the corresponding native enzyme. For instance, a modified CGL enzyme may contain a modified or mutant substrate recognition site that can be characterized based on the identity of the amino acid sequence of the modified or mutant substrate recognition site to that of an unmodified or native CGL enzyme from the same species or across species. For example, a modified human CGL enzyme characterized as having at least 90% identity to an unmodified human CGL enzyme means that at least 90% of the amino acids in the modified human CGL enzyme are identical to the amino acids in the unmodified human CGL enzyme.

An unmodified CGL enzyme may be a native CGL enzyme, particularly a human isoform or other primate isoforms. For example, the native human CGL enzyme may have the sequence of SEQ ID NO: 1. Non-limiting examples of other native primate CGL enzymes include *Pongo abelii* CGL (Genbank ID: NP_001124635.1; SEQ ID NO: 7), *Macaca fascicularis* CGL (Genbank ID: AAW71993.1; SEQ ID NO: 8), *Pan troglodytes* CGL (Genbank ID: XP_513486.2; SEQ ID NO: 9), and *Pan paniscus* CGL (Genbank ID: XP_003830652.1; SEQ ID NO: 10). Exemplary native CGL enzymes include a sequence having at least 90%, 95%, 96%, 97%, 98%, 99% or 100% identity (or any range derivable therein) of SEQ ID NOs: 1 or 7-10.

A native CGL may be modified by one or more other modifications, such as chemical modifications, substitutions, insertions, deletions, and/or truncations. Modifications may be at a substrate recognitions site of the native enzyme. A native CGL may be modified by substitutions. For example, the number of substitutions may be four, five, six, seven, or more. A native CGL may be modified in the substrate recognition site or any location that may affect substrate specificity. A modified polypeptide may have at least one amino acid substitution at amino acid positions corresponding to E59, S63, L91, R119, K268, T311, T336, E339, and/or 1353 of SEQ ID NO: 1 or amino acid positions of 59, 63, 91, 119, 268, 311, 336, 339, and/or 353 of a primate CGL. For example, the primate may be human, *Pongo abelii*, *Macaca fascicularis*, *Pan troglodyte*, or *Pan paniscus*. For example, an equivalent substitution of E59 in SEQ ID NO: 1 for SEQ ID NO: 7 would modify a valine and not glutamic acid as in SEQ ID NO: 1. Another contemplated substitution in SEQ ID NO: 7 is of V353, which is a isoleucine at the equivalent position in SEQ ID NO: 1 as illustrated in FIG. 6.

Substitutions in a modified CGL enzyme can occur at amino acid positions 59, 63, 91, 119, 268, 311, 339, and/or 353, and can be an aspartic acid (N), a valine (V), a leucine (L), a methionine (M), an arginine (R), a glycine (G), an alanine (A), or a serine (S). Modification can be one or more substitutions selected from the group consisting of E/V59N, E59I, S63L, L91M, R119L, R119A, R119D, R119H, R119G, K268R, T311G, T336D, T336E, E339V, and I/V353S. Substitutions may comprise a S63L, L91M, K268R, T311G, E339V, and I/V353S substitutions. Substitutions may comprise additional substitutions of either E/V59N or E/V59I; any one of R119L, R119A, R119D, R119H, and R119G; and/or either T336D or T336E.

Substitutions can be a combination of E59N, S63L, L91M, R119L, K268R, T311G, I353S, and E339V of human CGL (for example, the modified polypeptide having the amino acid sequence of SEQ ID NO: 3, a fragment or homolog thereof), a combination of E59I, S63L, L91M, R119L, K268R, T311G, E339V, and I353S of human CGL (for example, the modified polypeptide having the amino acid sequence of SEQ ID NO: 4, a fragment or homolog thereof), a combination of E59N, S63L, L91M, R119A, K268R, T311G, E339V, and I353S of human CGL (for example, the modified polypeptide having the amino acid sequence of SEQ ID NO: 5, a fragment or homolog thereof), a combination of E59I, S63L, L91M, R119A, K268R, T311G, E339V, and I353S of human CGL (for example, the modified polypeptide having the amino acid sequence of SEQ ID NO: 6, a fragment or homolog thereof), a combination of E59I, S63L, L91M, R119D, K268R, T311G, E339V, and I353S (for example, the modified polypeptide having the amino acid sequence of SEQ ID NO: 37, a fragment or homolog thereof), a combination of E59I, S63L, L91M, R119H, K268R, T311G, E339V, and I353S (for example, the modified polypeptide having the amino acid sequence of SEQ ID NO: 38, a fragment or homolog thereof), a combination of E59I, S63L, L91M, R119G, K268R, T311G, E339V, and I353S (for example, the modified polypeptide having the amino acid sequence of SEQ ID NO: 39, a fragment or homolog thereof), or any of these modifications of SEQ ID NOs: 2-6 and 37-39 in combination with either T336D or T336E. The modified CGL enzyme may be a *Pongo abelii* CGL-NLMLRGVS mutant (SEQ ID NO: 11), *Pongo abelii* CGL-ILMLRGVS mutant (SEQ ID NO: 12), *Pongo abelii* CGL-NLMARGVS mutant (SEQ ID NO: 13), *Pongo abelii* CGL-ILMARGVS mutant (SEQ ID NO: 14), *Pongo abelii* CGL-ILMDRGVS mutant (SEQ ID NO: 40), *Pongo abelii* CGL-ILMHRGVS mutant (SEQ ID NO: 41), *Pongo abelii* CGL-ILMGRGVS mutant (SEQ ID NO: 42), *Pongo abelii* CGL-NLMDRGVS mutant (SEQ ID NO: 52), *Pongo abelii* CGL-NLMHRGVS mutant (SEQ ID NO: 53), *Pongo abelii* CGL-NLMGRGVS mutant (SEQ ID NO: 54), *Macaca fascicularis* CGL-NLMLRGVS mutant (SEQ ID NO: 15), *Macaca fascicularis* CGL-ILMLRGVS mutant (SEQ ID NO: 16), *Macaca fascicularis*

CGL-NLMARGVS mutant (SEQ ID NO: 17), *Macaca fascicularis* CGL-ILMARGVS mutant (SEQ ID NO: 18), *Macaca fascicularis* CGL-ILMDRGVS mutant (SEQ ID NO: 43), *Macaca fascicularis* CGL-ILMHRGVS mutant (SEQ ID NO: 44), *Macaca fascicularis* CGL-ILMGRGVS mutant (SEQ ID NO: 45), *Macaca fascicularis* CGL-NLMDRGVS mutant (SEQ ID NO: 55), *Macaca fascicularis* CGL-NLMHRGVS mutant (SEQ ID NO: 56), *Macaca fascicularis* CGL-NLMGRGVS mutant (SEQ ID NO: 57), *Pan troglodytes* CGL-NLMLRGVS mutant (SEQ ID NO: 19), *Pan troglodytes* CGL-ILMLRGVS mutant (SEQ ID NO: 20), *Pan troglodytes* CGL-NLMARGVS mutant (SEQ ID NO: 21), *Pan troglodytes* CGL-ILMARGVS mutant (SEQ ID NO: 22), *Pan troglodytes* CGL-ILMDRGVS mutant (SEQ ID NO: 46), *Pan troglodytes* CGL-ILMHRGVS mutant (SEQ ID NO: 47), *Pan troglodytes* CGL-ILMGRGVS mutant (SEQ ID NO: 48), *Pan troglodytes* CGL-NLMDRGVS mutant (SEQ ID NO: 58), *Pan troglodytes* CGL-NLMHRGVS mutant (SEQ ID NO: 59), *Pan troglodytes* CGL-NLMGRGVS mutant (SEQ ID NO: 60), *Pan paniscus* CGL-NLMLRGVS mutant (SEQ ID NO: 23), *Pan paniscus* CGL-ILMLRGVS mutant (SEQ ID NO: 24), *Pan paniscus* CGL-NLMARGVS mutant (SEQ ID NO: 25), *Pan paniscus* CGL-ILMARGVS mutant (SEQ ID NO: 26), *Pan paniscus* CGL-ILMDRGVS mutant (SEQ ID NO: 49), *Pan paniscus* CGL-ILMHRGVS mutant (SEQ ID NO: 50), or *Pan paniscus* CGL-ILMGRGVS mutant (SEQ ID NO: 51), *Pan paniscus* CGL-NLMDRGVS mutant (SEQ ID NO: 61), *Pan paniscus* CGL-NLMHRGVS mutant (SEQ ID NO: 62), or *Pan paniscus* CGL-NLMGRGVS mutant (SEQ ID NO: 63).

A modified CGL enzyme can be linked to a heterologous amino acid sequence. For example, a modified CGL enzyme may be linked to the heterologous amino acid sequence as a fusion protein. The modified CGL enzyme may be linked to amino acid sequences, such as an IgG Fc, albumin, an albumin binding peptide, polysialic acid time extension, or an XTEN polypeptide for increasing the in vivo half-life.

To increase serum stability, the modified CGL enzyme may be linked to one or more polyether molecules. The polyether may be polyethylene glycol (PEG). The modified CGL enzyme may be linked to PEG via specific amino acid residues, such as lysine or cysteine. For therapeutic administration, such a polypeptide comprising the modified CGL enzyme may be dispersed in a pharmaceutically acceptable carrier.

A nucleic acid encoding a modified CGL enzyme is contemplated. The nucleic acid can be codon optimized for expression in bacteria, such as for *E. coli*. Nucleic acids that are codon optimized for the expression of the modified CGL enzymes provided in SEQ ID NOs: 37-39 in *E. coli* are provided in SEQ ID NOs: 64-66, respectively. The sequences provided in SED ID NOs: 64-66 encode an N-terminal 6x-Histidine tag. As such, the twelfth and following amino acids encoded by SEQ ID NOs: 64-66 corresponds to the second and following amino acids of SEQ ID NOs: 37-39, respectively. Alternatively, the nucleic acid can be codon optimized for expression in fungus (e.g., yeast), insects, or mammals. Further contemplated are vectors, such as expression vectors, containing such nucleic acids. A nucleic acid encoding the modified CGL enzyme can be operably linked to a promoter, including but not limited to heterologous promoters. A modified CGL enzyme may be delivered to a target cell by a vector (e.g., a gene therapy vector). Such vectors may have been modified by recombinant DNA technology to enable the expression of the modified CGL-encoding nucleic acid in the target cell.

These vectors may be derived from vectors of non-viral (e.g., plasmids) or viral (e.g., adenovirus, adeno-associated virus, retrovirus, lentivirus, herpes virus, or vaccinia virus) origin. Non-viral vectors may be complexed with agents to facilitate the entry of the DNA across the cellular membrane. Examples of such non-viral vector complexes include the formulation with polycationic agents, which facilitate the condensation of the DNA, and lipid-based delivery systems. Lipid-based delivery systems include liposome-based delivery of nucleic acids.

Host cells comprising such vectors are provided. The host cells may be bacteria (e.g., *E. coli*), fungal cells (e.g., yeast), insect cells, or mammalian cells.

A vector can be introduced into host cells for expressing the modified CGL enzyme. The proteins may be expressed in any suitable manner. The proteins may be expressed in a host cell such that the protein is glycosylated. Alternatively, the proteins may be expressed in a host cell such that the protein is aglycosylated.

Therapeutic formulations containing the modified CGL enzyme can be administered intravenously, intradermally, intraarterially, intraperitoneally, intramuscularly, subcutaneously, by infusion, by continuous infusion, via a catheter, in lipid compositions (e.g., liposomes). The subject may have been previously been treated for homocystinuria or hyperhomocysteinemia. The enzyme is administered to treat or ameliorate the recurrence of homocystinuria or hyperhomocysteinemia; the administration of the compound or compositions described herein can ameliorate one or more conditions and/or symptoms associated with homocystinuria and hyperhomocysteinemia. Known symptoms of homocystinuria include dislocation of the lenses in the eyes, nearsightedness, abnormal blood clots, osteoporosis, learning disabilities, developmental problems, chest deformities, scoliosis, megaloblastic anemia, and seizures. Known symptoms of hyperhomocysteinemia include blood clots, damage to the lining of blood vessels, dementia (e.g., Alzheimer's disease), and bone fractures.

The method may also comprise administering at least a second therapy to the subject, such as a second homocystinuria or hyperhomocysteinemia therapy. The second homocystinuria or hyperhomocysteinemia therapy may be a high-dose vitamin B6 or betaine (N,N,N-trimethylglycine) therapy.

A composition comprising a modified CGL enzyme or a nucleic acid encoding an modified CGL enzyme is provided for use in the treatment of homocystinuria or hyperhomocysteinemia in a subject. The use of a modified CGL enzyme or a nucleic acid encoding a modified CGL enzyme in the manufacture of a medicament for the treatment of homocystinuria or hyperhomocysteinemia is provided. The modified CGL enzyme may be any modified CGL enzyme disclosed herein.

Also provided herein are:
1. An isolated, modified primate cystathionine-γ-lyase (CGL) enzyme comprising at least the following substitutions relative to a native human CGL amino acid sequence (SEQ ID NO: 1), wherein the modified enzyme has both homocystinase and homocysteinase activity, said substitutions being selected from the group consisting of:
   (a) isoleucine at position 59, leucine at position 63, methionine at position 91, aspartic acid at position 119, arginine at position 268, glycine at position 311, valine at position 339, and serine at position 353;

(b) asparagine at position 59, leucine at position 119, aspartic acid at position 336, and valine at position 339;
(c) asparagine at position 59, leucine at position 63, methionine at position 91, leucine at position 119, arginine at position 268, glycine at position 311, aspartic acid at position 336, valine at position 339, and serine at position 353;
(d) isoleucine at position 59, leucine at position 63, methionine at position 91, leucine at position 119, arginine at position 268, glycine at position 311, aspartic acid at position 336, valine at position 339, and serine at position 353;
(e) asparagine at position 59, leucine at position 63, methionine at position 91, alanine at position 119, arginine at position 268, glycine at position 311, aspartic acid at position 336, valine at position 339, and serine at position 353;
(f) isoleucine at position 59, leucine at position 63, methionine at position 91, alanine at position 119, arginine at position 268, glycine at position 311, aspartic acid at position 336, valine at position 339, and serine at position 353;
(g) asparagine at position 59, leucine at position 119, glutamic acid at position 336, and valine at position 339;
(h) asparagine at position 59, leucine at position 63, methionine at position 91, leucine at position 119, arginine at position 268, glycine at position 311, glutamic acid at position 336, valine at position 339, and serine at position 353;
(i) isoleucine at position 59, leucine at position 63, methionine at position 91, leucine at position 119, arginine at position 268, glycine at position 311, glutamic acid at position 336, valine at position 339, and serine at position 353;
(j) asparagine at position 59, leucine at position 63, methionine at position 91, leucine at position 119, arginine at position 268, glycine at position 311, glutamic acid at position 336, valine at position 339, and serine at position 353;
(i) asparagine at position 59, leucine at position 63, methionine at position 91, alanine at position 119, arginine at position 268, glycine at position 311, glutamic acid at position 336, valine at position 339, and serine at position 353;
(k) isoleucine at position 59, leucine at position 63, methionine at position 91, alanine at position 119, arginine at position 268, glycine at position 311, glutamic acid at position 336, valine at position 339, and serine at position 353;
(l) isoleucine at position 59, leucine at position 63, methionine at position 91, histidine at position 119, arginine at position 268, glycine at position 311, valine at position 339, and serine at position 353; and
(m) isoleucine at position 59, leucine at position 63, methionine at position 91, glycine at position 119, arginine at position 268, glycine at position 311, valine at position 339, and serine at position 353.

2. The enzyme of claim 1, wherein the substitutions comprise asparagine at position 59, leucine at position 119, aspartic acid at position 336, and valine at position 339.

3. The enzyme of claim 2, wherein the substitutions further comprise leucine at position 63, methionine at position 91, arginine at position 268, glycine at position 311, and serine at position 353.

4. The enzyme of claim 1, wherein the substitutions comprise asparagine at position 59, leucine at position 119, glutamic acid at position 336, and valine at position 339.

5. The enzyme of claim 4, wherein the substitutions further comprise leucine at position 63, methionine at position 91, arginine at position 268, glycine at position 311, and serine at position 353.

6. The enzyme of claim 1, wherein the substitutions comprise isoleucine at position 59, leucine at position 63, methionine at position 91, aspartic acid at position 119, arginine at position 268, glycine at position 311, valine at position 339, and serine at position 353.

7. The enzyme of claim 1, wherein the substitutions comprise isoleucine at position 59, leucine at position 63, methionine at position 91, histidine at position 119, arginine at position 268, glycine at position 311, valine at position 339, and serine at position 353.

8. The enzyme of claim 1, wherein the substitutions comprise isoleucine at position 59, leucine at position 63, methionine at position 91, glycine at position 119, arginine at position 268, glycine at position 311, valine at position 339, and serine at position 353.

9. The enzyme of claim 1, wherein the modified CGL enzyme is a modified *Pongo abelii* CGL enzyme.

10. The enzyme of claim 9, wherein the modified *Pongo abelii* CGL enzyme comprises substitutions selected from the group consisting of:
(a) V59I, S63L, L91M, R119D, K268R, T311G, E339V, and V353S;
(b) V59N, R119L, T336D, and E339V;
(c) V59N, S63L, L91M, R119L, K268R, T311G, T336D, E339V, and V353S;
(d) V59I, S63L, L91M, R119L, K268R, T311G, T336D, E339V, and V353S;
(e) V59N, S63L, L91M, R119A, K268R, T311G, T336D, E339V, and V353S;
(f) V59I, S63L, L91M, R119A, K268R, T311G, T336D, E339V, and V353S;
(g) V59N, R119L, T336E, and E339V;
(h) V59N, S63L, L91M, R119L, K268R, T311G, T336E, E339V, and V353S;
(i) V59I, S63L, L91M, R119L, K268R, T311G, T336E, E339V, and V353S;
(j) V59N, S63L, L91M, R119A, K268R, T311G, T336E, E339V, and V353S;
(k) V59I, S63L, L91M, R119A, K268R, T311G, T336E, E339V, and V353S;
(l) V59I, S63L, L91M, R119H, K268R, T311G, E339V, and V353S; and
(m) V59I, S63L, L91M, R119G, K268R, T311G, E339V, and V353S.

11. The enzyme of claim 1, wherein the modified CGL enzyme is a modified human CGL enzyme, a modified *Macaca fascicularis* CGL enzyme, a modified *Pan troglodytes* CGL enzyme, or a modified *Pan paniscus* CGL enzyme.

12. The enzyme of claim 11, wherein the modified human CGL enzyme, the modified *Macaca fascicularis* CGL enzyme, the modified *Pan troglodytes* CGL enzyme, or the modified *Pan paniscus* CGL enzyme comprises substitutions selected from the group consisting of:
(a) E59I, S63L, L91M, R119D, K268R, T311G, E339V, and I353S;
(b) E59N, R119L, T336D, and E339V;
(c) E59N, S63L, L91M, R119L, K268R, T311G, T336D, E339V, and I353S;

(d) E59I, S63L, L91M, R119L, K268R, T311G, T336D, E339V, and I353S;
(e) E59N, S63L, L91M, R119A, K268R, T311G, T336D, E339V, and I353S;
(f) E59I, S63L, L91M, R119A, K268R, T311G, T336D, E339V, and I353S;
(g) E59N, R119L, T336E, and E339V;
(h) E59N, S63L, L91M, R119L, K268R, T311G, T336E, E339V, and I353S;
(i) E59I, S63L, L91M, R119L, K268R, T311G, T336E, E339V, and I353S;
(j) E59N, S63L, L91M, R119A, K268R, T311G, T336E, E339V, and I353S;
(k) E59I, S63L, L91M, R119A, K268R, T311G, T336E, E339V, and I353S;
(l) E59I, S63L, L91M, R119H, K268R, T311G, E339V, and I353S; and
(m) E59I, S63L, L91M, R119G, K268R, T311G, E339V, and I353S.

13. The enzyme of any one of claims 1-8, further comprising a heterologous peptide segment or a polysaccharide.

14. The enzyme of claim 13, wherein the heterologous peptide segment is an XTEN polypeptide, an IgG Fc, an albumin, or an albumin binding peptide.

15. The enzyme of claim 13, wherein the polysaccharide comprises polysialic acid polymers.

16. The enzyme of any one of claims 1-15, wherein the enzyme is coupled to a polyethylene glycol (PEG).

17. The enzyme of claim 16, wherein the enzyme is coupled to PEG via one or more lysine residues.

18. A nucleic acid comprising a nucleotide sequence encoding the enzyme of any one of claims 1-14.

19. The nucleic acid of claim 18, wherein the nucleic acid is codon optimized for expression in bacteria, fungus, insects, or mammals.

20. The nucleic acid of claim 19, wherein the bacteria are *E. coli*.

21. The nucleic acid of claim 20, wherein the nucleic acid comprises one of SEQ ID NOs: 64-66.

22. An expression vector comprising the nucleic acid of either claim 18 or 19.

23. A host cell comprising the nucleic acid of either claim 18 or 19.

24. The host cell of claim 23, wherein the host cell is a bacterial cell, a fungal cell, an insect cell, or a mammalian cell.

25. A therapeutic formulation comprising an enzyme of any one of claims 1-17 or a nucleic acid of either claim 18 or 19, in a pharmaceutically acceptable carrier.

26. A method of treating a subject having or at risk of developing homocystinuria or hyperhomocysteinemia comprising administering to the subject a therapeutically effective amount of the formulation of claim 25.

27. A method of treating a subject having or at risk of developing homocystinuria or hyperhomocysteinemia, the method comprising:
administering to the subject a therapeutically effective amount of a formulation of claim 25 or of a formulation comprising an isolated, modified primate cystathionine-γ-lyase (CGL) enzyme having substitutions relative to a native human CGL amino acid sequence (SEQ ID NO: 1) or a nucleic acid comprising a nucleotide sequence encoding the modified enzyme, said substitutions being selected from the group consisting of:

(a) asparagine at position 59, leucine at position 119, and valine at position 339;
(b) valine at position 59, leucine at position 119, and valine at position 339;
(c) asparagine at position 59, leucine at position 63, methionine at position 91, leucine at position 119, arginine at position 268, glycine at position 311, valine at position 339, and serine at position 353;
(d) isoleucine at position 59, leucine at position 63, methionine at position 91, leucine at position 119, arginine at position 268, glycine at position 311, valine at position 339, and serine at position 353;
(e) asparagine at position 59, leucine at position 63, methionine at position 91, alanine at position 119, arginine at position 268, glycine at position 311, valine at position 339, and serine at position 353; and
(f) isoleucine at position 59, leucine at position 63, methionine at position 91, alanine at position 119, arginine at position 268, glycine at position 311, valine at position 339, and serine at position 353.

28. The method of claim 27, wherein the modified CGL enzyme is a modified *Pongo abelii* CGL enzyme.

29. The method of claim 28, wherein the modified *Pongo abelii* CGL enzyme comprises substitutions selected from the group consisting of:
(a) V59N, R119L, and E339V;
(b) R119L, and E339V;
(c) V59N, S63L, L91M, R119L, K268R, T311G, E339V, and V353S;
(d) V59I, S63L, L91M, R119L, K268R, T311G, E339V, and V353S;
(e) V59N, S63L, L91M, R119A, K268R, T311G, E339V, and V353S; and
(f) V59I, S63L, L91M, R119A, K268R, T311G, E339V, and V353S.

30. The method of claim 27, wherein the modified CGL enzyme is a modified human CGL enzyme, a modified *Macaca fascicularis* CGL enzyme, a modified *Pan troglodytes* CGL enzyme, or a modified *Pan paniscus* CGL enzyme.

31. The method of claim 30, wherein the modified human CGL enzyme, the modified *Macaca fascicularis* CGL enzyme, the modified *Pan troglodytes* CGL enzyme, or the modified *Pan paniscus* CGL enzyme comprises substitutions selected from the group consisting of:
(a) E59N, R119L, and E339V;
(b) E59V, R119L, and E339V;
(c) E59N, S63L, L91M, R119L, K268R, T311G, E339V, and I353S;
(d) E59I, S63L, L91M, R119L, K268R, T311G, E339V, and I353S;
(e) E59N, S63L, L91M, R119A, K268R, T311G, E339V, and I353S; and
(f) E59I, S63L, L91M, R119A, K268R, T311G, E339V, and I353S.

32. The method of any one of claims 27-31, wherein the enzyme further comprises a heterologous peptide segment.

33. The method of claim 32, wherein the heterologous peptide segment is an XTEN polypeptide, an IgG Fc, an albumin, an albumin binding peptide, or polysialic acid time extension.

34. The method of any one of claims 27-31, wherein the enzyme is coupled to polyethylene glycol (PEG).

35. The method of claim 34, wherein the enzyme is coupled to PEG via one or more lysine or cysteine residues.

36. The method of claim 27, wherein the subject is maintained on a methionine-restricted diet.
37. The method of claim 27, wherein the subject is maintained on a normal diet.
38. The method of claim 27, wherein the subject is a human patient.
39. The method of claim 27, wherein the formulation is administered intravenously, intraarterially, intraperitoneally, intralesionally, intraarticularly, intraprostaticaly, intrapleurally, intratracheally, intravitreally, intramuscularly, intravesicularlly, intraumbilically, by injection, by infusion, by continuous infusion, by localized perfusion bathing target cells directly, or via a catheter.
40. The method of claim 27, wherein the subject has previously been treated for homocystinuria or hyperhomocysteinemia and the enzyme is administered to prevent the recurrence of homocystinuria or hyperhomocysteinemia.
41. The method of claim 27, further comprising administering at least a second homocystinuria or hyperhomocysteinemia therapy to the subject.
42. The method of claim 41, wherein the second homocystinuria or hyperhomocysteinemia therapy is a high-dose vitamin B6 or betaine (N,N,N-trimethylglycine) therapy.
43. The therapeutic formulation of claim 25 for use as a medicament in the treatment of a subject having homocystinuria or hyperhomocysteinemia.
44. The enzyme of any one of claims 1-14 for use in the treatment of homocystinuria or hyperhomocysteinemia in a subject.

As used herein the terms "encode" or "encoding," with reference to a nucleic acid, are used to make the invention readily understandable by the skilled artisan; however, these terms may be used interchangeably with "comprise" or "comprising," respectively.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used here, the term "about" is understood by persons of ordinary skill in the art and will vary to some extent on the context in which it is used. Generally, about encompasses a range of values that are plus/minus 10% of a referenced value.

BRIEF DESCRIPTION OF THE DRAWINGS

The following drawings form part of the present specification and are included to further exemplify the methods, compounds, and composition described.

FIG. 6—Sequence alignment of SEQ ID NOs: 1 and 7-10. Asterisks indicate engineered positions in various of the modified CGL enzymes.

DETAILED DESCRIPTION

Figure 1:
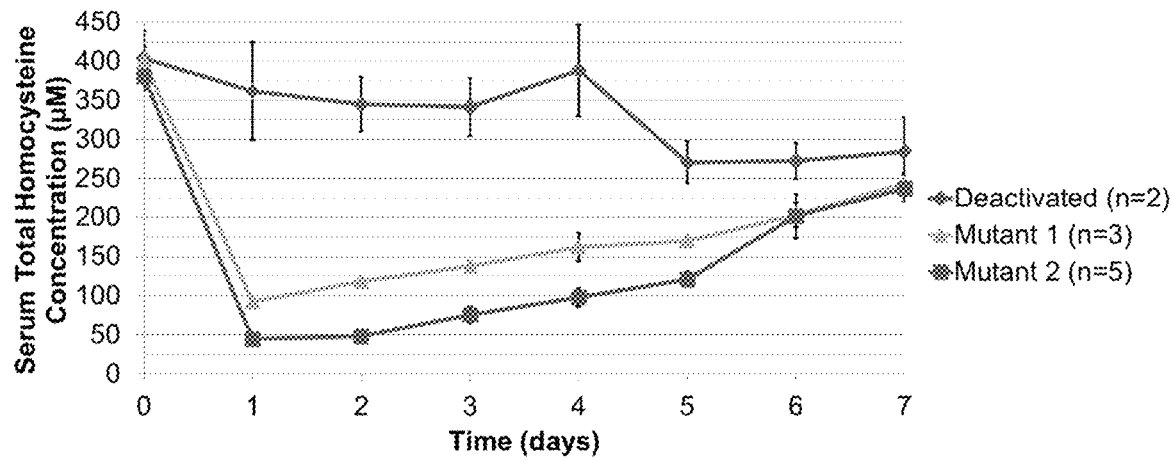
FIG. 1—Evaluation of Modified CGL in vivo. Enzyme was dosed a single time at 50 mg/kg (i.p.). Mutant 1 corresponds to hCGL-NLV (SEQ ID NO: 2) and mutant 2 corresponds to hCGL-8mut-4 (SEQ ID NO: 6). Serum was collected prior to the injection and every 24 hours post injection for a week.

Methods are provided of using modified, therapeutic enzymes that degrade homocysteine and homocystine to treat diseases, such as homocystinuria and hyperhomocysteinemia. The therapeutic enzymes include the hCGL-NLV mutant (E59N, R119L, E339V) as well as recombinantly engineered human cystathionine-γ-lyase (hCGL) enzymes with improved homocyst(e)inase activity relative to the hCGL-NLV mutant. Mutants displaying higher catalytic activity require lower concentrations of therapeutic agent for dosing of patients.

I. Definitions

As used herein the terms "enzyme" and "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide to fall by half in vitro (e.g., as measured in cell culture media) or in vivo (e.g., as measured in serum), for example, after injection in a mammal. Methods to measure "half-life" include the use of antibodies specific for CGL or PEG used in an ELISA (enzyme-linked immunosorbent assay) format such that the physical amount of protein is measured as a function of time. Other methods germane to measuring the half-life include determining the catalytic activity of the enzyme drug as a function of time by any assay that detects the production of any substrates resulting from conversion of homocyst(e)ine, to products such as alpha-ketobutyrate, methanethiol, and/or ammonia.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical or wild-type form of a gene, a gene product, or a characteristic of that gene or gene product when isolated from a naturally occurring source. In contrast, the term "modified," "variant," "mutein," or "mutant" refers to a gene or gene product that displays modification in sequence and functional properties (i.e., altered characteristics) when compared to the native gene or gene product, wherein the modified gene or gene product is genetically engineered and not naturally present or occurring.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well.

The term "therapeutically effective amount" as used herein refers to an amount of a therapeutic composition (i.e., a modified CGL enzyme or a nucleic acid encoding such an enzyme) that is employed in methods to achieve a therapeutic effect, i.e., to deplete homocyst(e)ine in a patient's circulation to a level that is at or below a normal reference value. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease, such as elevated (e.g., above 15 μmon) serum levels of total homocysteine. The dosage ranges for the administration of therapeutic compositions are those large enough to produce the desired effect in which the symptoms of homocystinuria are reduced. For example, a therapeutically effective amount of a therapeutic composition may be an amount such that when administered in a physiologically tolerable composition is sufficient to achieve an intravascular (plasma) concentration of from about 0.001 to about 100 units (U) per mL, preferably above about 0.1 U, and more preferably above 1.0 U modified CGL enzyme per mL. Typical dosages can be administered based on body weight, and are in the range of about 1-100 U/kilogram (kg)/day, preferably about 2-25 U/kg/day, and more preferably about 2.0-8.0 U/kg/day. An exemplary amount can be 5.0 U/kg/day or 35 U/kg/week. The dosage should not be so large as to cause adverse side effects, such as hyperviscosity syndromes, pulmonary edema, congestive heart failure, and the like. Generally, the dosage will vary with age of, condition of, sex of, and extent of the disease in the patient and can be determined by one of skill in the art. The dosage can be adjusted by the individual physician in the event of any complication. The dosage should result in the tHcy content in a subject's serum being reduced at least by 50%, at least by 60%, and at least by 70% in about 12 to 24 hours. The dosage could result in the tHcy content in a subject's serum being reduced at least 50% to 70% in 6 hours. The dosage resulting in a statistically significant response should result in the tHcy content in the subject's serum being reduced to a level within two standard deviations of the reference level disclosed in Nygard et al. (1998). As such, the dosage could result in the tHcy content in the subject's serum being reduce to a level less than 20-25 μM.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "cystathionine-γ-lyase" (CGL or cystathionase) refers to any enzyme that catalyzes the hydrolysis of cystathionine to cysteine. As used herein, the terms also contemplate primate forms of cystathionine-γ-lyase (or cystathionine-gamma-lyase), including the human form of cystathionine-γ-lyase.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a therapeutically effective amount of a homocyst(e)inase.

"Subject" and "patient" refer to either a human or non-human, such as primates, mammals, and vertebrates. The subject may be a human.

II. Cystathionine-γ-Lyase

A lyase is an enzyme that catalyzes the breaking of various chemical bonds, often forming a new double bond or a new ring structure. For example, an enzyme that catalyzes this reaction would be a lyase: ATP→cAMP+PPi. Lyases differ from other enzymes in that they only require one substrate for the reaction in one direction, but two substrates for the reverse reaction.

A number of pyrioxal-5'-phosphate (PLP)-dependent enzymes are involved in the metabolism of cysteine, homocysteine, and methionine, and these enzymes form an evolutionarily related family, designated as Cys/Met metabolism PLP-dependent enzymes. These enzymes are proteins of about 400 amino acids and the PLP group is attached to a lysine residue located in the central location of the polypeptide. Members of this family include cystathionine-γ-lyase (CGL), cystathionine-γ-synthase (CGS), cystathionine-β-lyase (CBL), methionine-γ-lyase (MGL), and O-acetylhomoserine (OAH)/O-acetyl-serine (OAS) sulfhydrylase (OSHS). Common to all of them is the formation of a Michaelis complex leading to an external substrate aldimine. The further course of the reaction is determined by the substrate specificity of the particular enzyme.

For example, the inventors introduced specific mutations into a PLP-dependent lyase family member, such as the human cystathionine-γ-lyase, to change its substrate specificity. In this manner the inventors produced novel variants with the de novo ability to degrade homocyst(e)ine as a substrate with higher catalytic activity than hGGL-NLV. A modification of other PLP-dependent enzymes for producing novel homocyst(e)ine degrading activity may also be contemplated.

CGL is a tetramer that catalyzes the last step in the mammalian transsulfuration pathway (Rao et al., 1990). CGL catalyzes the conversion of L-cystathionine to L-cysteine, alpha-ketobutyrate, and ammonia. Pyridoxal phosphate is a prosthetic group of this enzyme. Protein engineering was used to convert cystathionase, which has only weak activity for the degradation of homocysteine and homocystine, into an enzyme that can degrade homocysteine and homocystine at a high rate (U.S. Pat. No. 9,481,877, which is incorporated herein by reference in its entirety).

III. HOMOCYST(E)INASE ENGINEERING

Since humans do not produce homocyst(e)inase it is necessary to engineer homocyst(e)inase for human therapy that have high activity and specificity for degrading homocyst(e)ine under physiological conditions, as well as high stability in physiological fluids, such as serum, and are also non-immunogenic because they are native proteins that normally elicit immunological tolerance.

Due to the undesired immunogenic effects seen in animal studies with pMGL (MGL from *P. putida*), it is desirable to engineer homocyst(e)ine degradation activity in a human enzyme. Immunological tolerance to human proteins makes it likely that such an enzyme will be non-immunogenic or minimally immunogenic and therefore well tolerated.

Although mammals do not have a homocyst(e)inase, they do have a cystathionine-γ-lyase (CGL). CGL is a tetramer that catalyzes the last step in the mammalian transsulfuration pathway (Rao et al., 1990). CGL catalyzes the conversion of L-cystathionine to L-cysteine, alpha-ketobutyrate, and ammonia. The human CGL (hCGL) cDNA had previously been cloned and expressed, but with relatively low yields (~5 mg/L culture) (Lu et al., 1992; Steegborn et al., 1999).

As such, there are provided methods and compositions related to a primate (particularly human) cystathionine-γ-lyase (CGL or cystathionase) modified via mutagenesis to hydrolyze homocyst(e)ine with high efficiency.

Described are modified CGL enzymes that exhibit at least one functional activity that is comparable to an unmodified CGL enzyme. A modified CGL enzyme may be further modified to increase serum stability. Modified CGL enzymes include, for example, a protein that possesses an additional advantage, such as the homocyst(e)inase enzyme activity, compared to the unmodified CGL enzyme. The unmodified protein or polypeptide may be a native cystathionine-γ-lyase, such as a human cystathionine-γ-lyase.

Determination of activity may be achieved using assays familiar to those of skill in the art, particularly with respect to the enzyme's activity, and may include for comparison purposes, for example, the use of native and/or recombinant versions of either the modified or unmodified enzyme. For example, the homocyst(e)inase activity may be determined by any assay to detect the production of any substrates resulting from conversion of homocyst(e)ine, such as alpha-ketobutyrate, methanethiol, and/or ammonia.

A modified CGL enzyme, may be identified based on its increase in homocyst(e)ine degrading activity. For example, substrate recognition sites of the unmodified polypeptide may be identified. This identification may be based on structural analysis or homology analysis. A population of mutants involving modifications of such substrate recognitions sites may be generated. Mutants with increased homocyst(e)ine degrading activity may be selected from the mutant population. Selection of desired mutants may include methods, such as detection of byproducts or products from homocyst(e)ine degradation.

Modified CGL enzymes may possess deletions and/or substitutions of amino acids; thus, an enzyme with a deletion, an enzyme with a substitution, and an enzyme with a deletion and a substitution are modified CGL enzymes. These modified CGL enzymes may further include insertions or added amino acids, such as with fusion proteins or proteins with linkers, for example. A "modified deleted CGL enzyme" lacks one or more residues of the native enzyme, but may possess the specificity and/or activity of the native enzyme. A modified deleted CGL enzyme may also have reduced immunogenicity or antigenicity. An example of a modified deleted CGL enzyme is one that has an amino acid residue deleted from at least one antigenic region, that is, a region of the enzyme determined to be antigenic in a particular organism, such as the type of organism that may be administered the modified CGL enzyme.

Substitution or replacement variants may contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine;

phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified CGL enzyme may possess an insertion of residues, which typically involves the addition of at least one residue in the enzyme. This may include the insertion of a targeting peptide or polypeptide or simply a single residue. Terminal additions, called fusion proteins, are discussed below.

The term "biologically functional equivalent" is well understood in the art and is further defined in detail herein. Accordingly, CGL enzyme sequences that have about 90% or more sequence identity to SEQ ID NO: 1, or even between about 91% and about 99% of amino acids (including 92%, 93%, 94%, 95%, 96%, 97%, 98%, and 99%) that are identical to or conservative substitution of the amino acids of an modified CGL enzyme disclosed herein are included, provided the biological activity of the enzyme is maintained such that a measureable biological activity parameter (e.g., conversion of homocyst(e)ine to alpha-ketobutyrate, methanethiol, and ammonia) is within about 20%, about 15%, about 10%, or about 5% of a modified CGL enzyme disclosed herein. A modified CGL enzyme may be biologically functionally equivalent to its unmodified counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Figure 6:
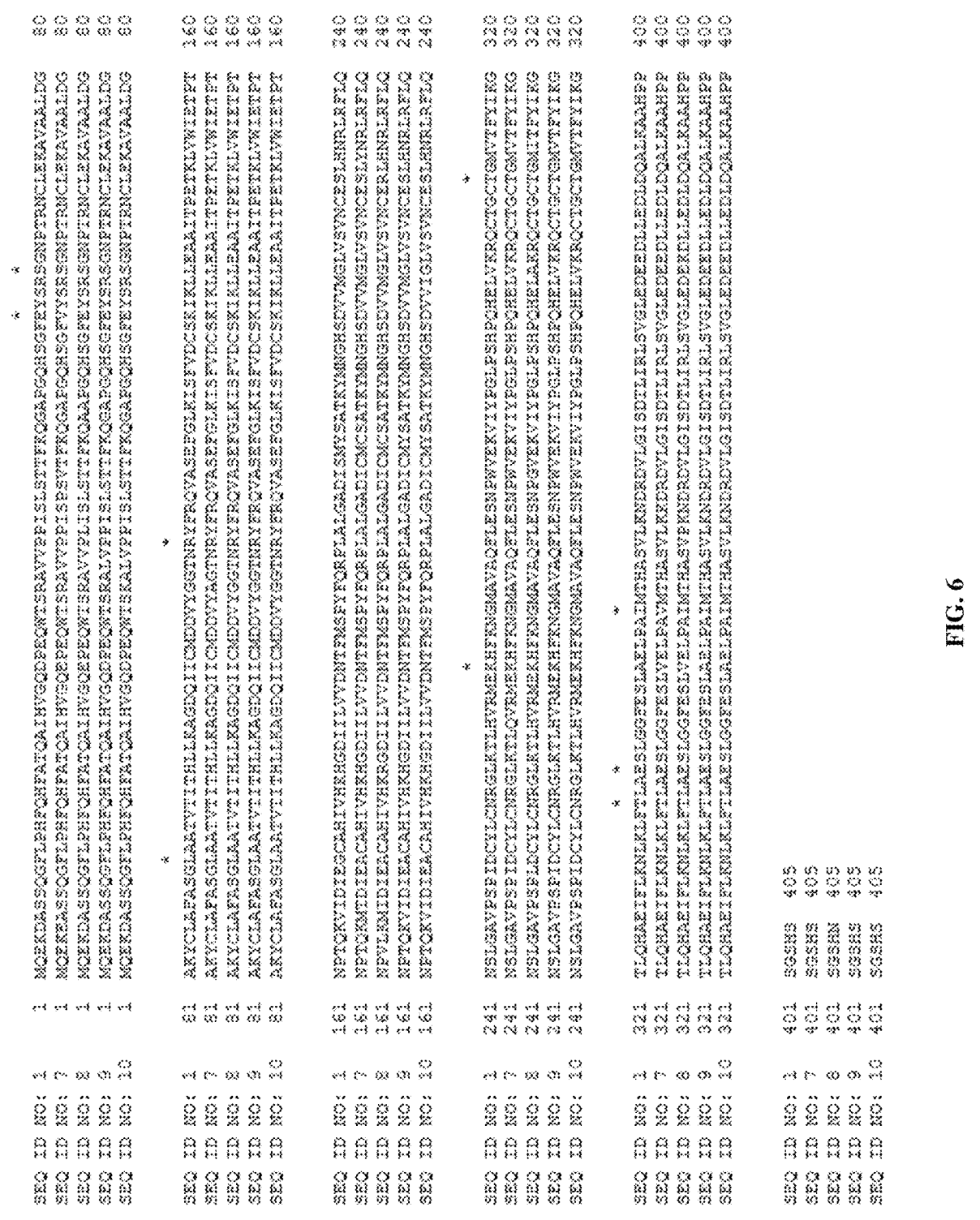

In particular, five amino acid positions in addition to the three mutation sites (i.e. E59N-R119L-E339V) were found to confer improved activity compared to hCGL-NLV (SEQ ID NO: 2). These additional positions are located at hCGL (SEQ ID NO: 1) residues 63, 91, 268, 311, and 353 (see, FIG. 6). Mutation of one or more of these positions to S63L, L91M, K268R, T311G, and I353S, in combination with mutations of residues at positions 59, 119, and 339, resulted in improved activity compared to hCGL-NLV. In particular, the variants contained amino acid substitutions corresponding to SEQ ID NO: 3, hCGL-E59N-S63L-L91M-R119L-K268R-T311G-E339V-I353S (hCGL-Smut-1); SEQ ID NO: 4, hCGL-E59I-563L-L91M-R119L-K268R-T311G-E339V-I353S (hCGL-Smut-2); SEQ ID NO: 5, hCGL-E59N-S63L-L91M-R119A-K268R-T311G-E339V-I353S (hCGL-Smut-3); SEQ ID NO: 6, hCGL-E59I-563L-L91M-R119A-K268R-T311G-E339V-I353S (hCGL-Smut-4); SEQ ID NO: 27, hCGL-E59N-R119L-T336D-E339V (hCGL-NLDV); SEQ ID NO: 28, hCGL-E59N-563L-L91M-R119L-K268R-T311G-T336D-E339V-I353S (hCGL-9mutD-1); SEQ ID NO: 29, hCGL-E59I-563L-L91M-R119L-K268R-T311G-T336D-E339V-I353S (hCGL-9mutD-2); SEQ ID NO: 30, hCGL-E59N-S63L-L91M-R119A-K268R-T311G-T336D-E339V-I353S (hCGL-9mutD-3); SEQ ID NO: 31, hCGL-E59I-563L-L91M-R119A-K268R-T311G-T336D-E339V-I353S (hCGL-9mutD-4); SEQ ID NO: 32, hCGL-E59N-R119L-T336E-E339V (hCGL-NLEV); SEQ ID NO: 33, hCGL-E59N-S63L-L91M-R119L-K268R-T311G-T336E-E339V-I353S (hCGL-9mutE-1); SEQ ID NO: 34, hCGL-E59I-563L-L91M-R119L-K268R-T311G-T336E-E339V-I353S (hCGL-9mutE-2); SEQ ID NO: 35, hCGL-E59N-563L-L91M-R119A-K268R-T311G-T336E-E339V-I353S (hCGL-9mutE-3); SEQ ID NO: 36, hCGL-E59I-563L-L91M-R119A-K268R-T311G-T336E-E339V-I353S (hCGL-9mutE-4); SEQ ID NO: 37, hCGL-E59I-563L-L91M-R119D-K268R-T311G-E339V-I353S (Mutant 3); SEQ ID NO: 38, hCGL-E59I-563L-L91M-R119H-K268R-T311G-E339V-I353S (Mutant 4); and SEQ ID NO: 39, hCGL-E59I-563L-L91M-R119G-K268R-T311G-E339V-I353S (Mutant 5).

IV. ENZYMATIC HOMOCYST(E)INE DEPLETION FOR THERAPY

The polypeptides may be used for the treatment of diseases, such as homocystinuria, with novel enzymes that deplete homocystine and/or homocysteine. Disclosed are treatment methods using modified CGL with L-cyst(e)ine degrading activity. Enzymes with homocyst(e)ine degrading activity for increased therapeutic efficacy are provided.

Provided are modified CGL enzymes with homocyst(e)ine degrading activity for treating diseases, such as homocystinuria. Particularly, the modified polypeptide may have human polypeptide sequences and thus may prevent adverse immunogenic reactions when administered to human patients, allow repeated dosing, and increase the therapeutic efficacy.

Depletion can be conducted in vivo in the circulation of a mammal, in vitro in cases where homocyst(e)ine depletion in tissue culture or other biological mediums is desired, and in ex vivo procedures where biological fluids, cells, or tissues are manipulated outside the body and subsequently returned to the body of the patient mammal. Depletion of homocyst(e)ine from circulation, culture media, biological fluids, or cells is conducted to reduce the amount of homocyst(e)ine accessible to the material being treated, and therefore comprises contacting the material to be depleted with a homocyst(e)ine-depleting amount of the engineered enzyme under homocyst(e)ine-depleting conditions as to degrade the ambient homocyst(e)ine in the material being contacted.

Homocyst(e)ine-depleting efficiency can vary widely depending upon the application, and typically depends upon the amount of homocyst(e)ine present in the material, the desired rate of depletion, and the tolerance of the material for exposure to homocyst(e)inase. Homocyst(e)ine levels in a material, and therefore rates of homocyst(e)ine depletion from the material, can readily be monitored by a variety of chemical and biochemical methods well known in the art. Exemplary homocyst(e)ine-depleting amounts are described further herein, and can range from 0.001 to 100 units (U) of engineered enzyme, preferably about 0.01 to 10 U, and more preferably about 0.1 to 5 U engineered enzyme per milliliter (mL) of material to be treated.

Homocyst(e)ine-depleting conditions are buffer and temperature conditions compatible with the biological activity of a homocyst(e)inase enzyme, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

The contacting in vivo may be accomplished by administering, by intravenous or intraperitoneal injection, a therapeutically effective amount of a physiologically tolerable composition comprising a modified CGL enzyme to a patient, thereby depleting the circulating homocyst(e)ine present in the patient.

The modified CGL enzyme can be administered parenterally by injection or by gradual infusion over time. The modified CGL enzyme can be administered intravenously, intraperitoneally, intramuscularly, can be injected directly into the tissue containing the tumor cells, or can be administered by a pump connected to a catheter that may contain a potential biosensor or homocyst(e)ine.

The therapeutic compositions containing modified CGL enzyme are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of modified CGL enzyme and conversely low serum and tissue levels of homocyst(e)ine. Alternatively, continuous intravenous infusion sufficient to maintain concentrations in the blood in the ranges specified for in vivo therapies are contemplated. Notably, the weekly dosage of modified CGL enzymes for the treatment of homocystinuria and hyperhomocysteinemia is about one-fourth of the weekly dosage required for the treatment of cancer. U.S. Pat. No. 9,481,877.

V. CONJUGATES

The compositions and methods provided involve further modification of the modified CGL enzyme for improvement, such as by forming conjugates with heterologous peptide segments or polymers, such as polyethylene glycol. The modified CGL enzyme may be linked to PEG to increase the hydrodynamic radius of the enzyme and hence increase the serum persistence. The disclosed polypeptide may be conjugated to any targeting agent, such as a ligand having the ability to specifically and stably bind to an external receptor or binding site on a tumor cell (U.S. Patent Publ. 2009/0304666). The PEG can be from about 3,000 to 20,000 Daltons in size, with an exemplary size being 5,000 Daltons.

A. Fusion Proteins

Fusion proteins are provided in which the modified CGL enzyme may be linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

The modified CGL enzyme may be linked to a peptide that increases the in vivo half-life, such as an XTEN polypeptide (Schellenberger et al., 2009), IgG Fc domain, albumin, or an albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

The modified CGL enzyme may be chemically conjugated using bifunctional cross-linking reagents or fused at the protein level with peptide linkers. Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the modified CGL enzyme, such as Gly-Ser linkers.

Homobifunctional reagents that carry two identical functional groups may induce cross-linking between identical and different macromolecules or subunits of a macromolecule, and link polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become popular because of their commercial availability, ease of synthesis, and the mild reaction conditions under which they can be applied.

Some heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine modified CGL enzymes, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Flexible linkers may also be used.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

Methods and compositions related to PEGylation of modified CGL enzyme are disclosed. For example, the modified CGL enzyme may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70% active, the amount of PEG used should ensure that only active PEG molecules are counted in the protein-to-PEG reaction stoichiometry.

VI. PROTEINS AND PEPTIDES

Compositions comprising at least one protein or peptide, such as a modified CGL enzyme, are provided. These peptides may be comprised in a fusion protein or conjugated to an agent as described supra.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

Accordingly, the term "protein or peptide" encompasses amino acid sequences comprising at least one of the 20 common amino acids found in naturally occurring proteins, or at least one modified or non-natural amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VII. NUCLEIC ACIDS AND VECTORS

Nucleic acid sequences encoding a modified CGL enzyme or a fusion protein containing a modified CGL enzyme are disclosed. Depending on which expression system is used, nucleic acid sequences can be selected based on conventional methods. For example, if the modified CGL enzyme is derived from human cystathionase and contains multiple codons that are rarely utilized in *E. coli*, then that may interfere with expression. Therefore, the respective genes or variants thereof may be codon optimized for *E. coli* expression using freely available software (see Hoover & Lubkowski, 2002) to design coding sequences free of rare codons. Various vectors may be also used to express the protein of interest, such as a modified CGL enzyme. Exemplary vectors include, but are not limited, plasmid vectors, viral vectors, transposon, or liposome-based vectors.

VIII. HOST CELLS

Host cells may be any that may be transformed to allow the expression and secretion of modified CGL enzyme and conjugates thereof. The host cells may be bacteria, mammalian cells, yeast, or filamentous fungi. Various bacteria include *Escherichia* and *Bacillus*. Yeasts belonging to the genera *Saccharomyces, Kiuyveromyces, Hansenula,* or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus,* and *Pyricularia*.

Examples of usable host organisms include bacteria, e.g., *Escherichia coli* MC1061, derivatives of *Bacillus subtilis* BRB 1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; American Type Culture Collection (ATCC) No. CCL61), rat pituitary cells (GH1; ATCC No. CCL82), HeLa S3 cells (ATCC No. CCL2.2), rat hepatoma cells (H-4-II-E; ATCC No. CRL-1548), SV40-transformed monkey kidney cells (COS-1; ATCC No. CRL-1650), and murine embryonic cells (NIH-3T3; ATCC No. CRL-1658). The foregoing is meant to be illustrative but not limitative of the many possible host organisms known in the art. In principle, all hosts capable of secretion can be used whether prokaryotic or eukaryotic.

Mammalian host cells expressing the modified CGL enzymes and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

IX. PROTEIN PURIFICATION

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulfate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

A protein or peptide may be isolated or purified, for example, a modified CGL enzyme, a fusion protein containing the modified CGL enzyme, or a modified CGL enzyme post PEGylation. For example, a His tag or an affinity epitope may be comprised in such a modified CGL enzyme to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

X. THERAPEUTIC COMPOSITIONS

The human cystathionine-γ-lyase gene contains multiple codons that are rarely utilized in *E. coli* and can interfere with expression. Thus, in order to optimize protein expression in *E. coli*, the respective genes may be assembled with codon optimized oligonucleotides designed using DNAWorks software (Hoover et al., 2002). Each construct may contain an N-terminal NcoI restriction site, an in-frame N-terminal His6 tag, and a C-terminal EcoRI site for simplifying cloning. After cloning into a pET28a vector (Novagen), *E. coli* (BL21) containing an appropriate cystathionase expression vector may be grown at 37° C. using Terrific Broth (TB) media containing 50 μg/mL kanamycin in shaker flasks at 250 rpm until reaching an $OD_{600}$ of ~0.5-0.6. At this point the cultures may be switched to a shaker at 25° C., induced with 0.5 mM IPTG, and allowed to express protein for an additional 12 h. Cell pellets may be then collected by centrifugation and re-suspended in an IMAC buffer (10 mM NaPO$_4$/10 mM imidazole/300 mM NaCl, pH 8). After lysis by a French pressure cell, lysates may be centrifuged at 20,000×g for 20 min at 4° C., and the resulting supernatant applied to a nickel IMAC column, washed extensively (90-100 column volumes) with an IMAC buffer containing 0.1% TRITON® 114, washed with 10-20 column volumes of IMAC buffer, and then eluted with an IMAC elution buffer (50 mM NaPO$_4$/250 mM imidazole/300 mM NaCl, pH 8). The purified protein was subjected to buffer exchange into a 100 mM NaPO$_4$ buffer at pH 8.3 using a 10,000 MWCO (molecule weight cut off) filtration device (Amicon). Fractions containing enzyme may be then incubated with 10 mM pyridoxal-5'-phosphate (PLP) for an hour at 25° C. Methoxy PEG Succinimidyl Carboxymethyl Ester 5000 MW (JenKem Technology) was then added to hCGL-8mut-1 at an 80:1 molar ratio and allowed to react for 1 h at 25° C. under constant stirring. The resulting mixture was extensively buffer exchanged (PBS with 10% glycerol) using a 100,000 MWCO filtration device (Amicon), and sterilized with a 0.2 micron syringe filter (VWR). Enzyme aliquots may be then flash frozen in liquid nitrogen and stored at −80° C. CGL and CGL variants purified in this manner should be >95% homogeneous as assessed by SDS-PAGE and coomassie staining. The yield may be calculated based upon the calculated extinction coefficient, $\lambda_{280}$=29,870 M$^{-1}$ cm$^{-1}$ in a final buffer concentration of 6 M guanidinium hydrochloride, 20 mM phosphate buffer, pH 6.5 (Gill and von Hippel, 1989).

As an example, the serum stability of PEGylated hCGL-8mut-1 was tested by incubation of the enzyme in pooled human serum at 37° C. at a final concentration of 10 μm. At different time points, aliquots were withdrawn and tested for activity using the DTNB (Ellman's Reagent; 5,5-dithio-bis-(2-nitrobenzoic acid)) assay as described in U.S. Pat. Publ. 2011/0200576, which is incorporated herein by reference in its entirety. PEGylated hCGL-8mut-1 was calculated to have a half-life (T05) of 101±4 h.

No limitation as to the particular nature of the therapeutic preparation is intended. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, for use as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare therapeutic compositions comprising proteins, antibodies, and drugs in a form appropriate for the intended application. Generally, therapeutic compositions may comprise an effective amount of one or more modified CGL enzymes or additional agents dissolved or dispersed in a pharmaceutically acceptable carrier. The phrases "therapeutic or therapeutically acceptable" refers to molecular entities and compositions that do not produce an adverse, allergic, or other untoward reaction when administered to an animal, such as, for example, a human, as appropriate. The preparation of a therapeutic composition that contains at least one modified CGL enzyme isolated by the method disclosed herein, or additional active ingredient will be known to those of skill in the art, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, surfactants, antioxidants, preservatives (e.g., antibacterial agents, antifungal agents), isotonic agents, absorption delaying agents, salts, preservatives, drug stabilizers, gels, binders, excipients, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the therapeutic compositions is contemplated.

The compositions can be administered subcutaneously, intravenously, intraarterially, intraperitoneally, intramuscularly, by injection, by infusion, by continuous infusion, via a catheter, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Therapeutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations may be administered in a variety of dosage forms, such as being formulated for parenteral administrations, such as injectable solutions, or aerosols for delivery to the lungs, or formulated for alimentary administrations, such as drug release capsules and the like.

The disclosed compositions suitable for administration may be provided in a pharmaceutically acceptable carrier with or without an inert diluent. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

The disclosed compositions can be combined with the carrier in any convenient and practical manner, i.e., by solution, suspension, emulsification, admixture, encapsulation, absorption, and the like.

The use of a therapeutic lipid vehicle composition that includes a modified CGL enzyme, one or more lipids, and an aqueous solvent, is provided. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the modified CGL enzyme or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or a therapeutically effective amount may vary according to the response of the subject. The practitioner responsible for administration will, in any event, determine the concentration of active ingredient(s) in a composition and appropriate dose(s) for the individual subject.

Therapeutic compositions may comprise, for example, at least about 0.1% of an active compound. An active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such therapeutic formulations, and as such, a variety of dosages and treatment regimens may be desirable.

A dose may also comprise from about 500 microgram/kg body weight, about 1 milligram/kg body weight, about 5 milligram/kg body weight, about 10 milligram/kg body weight, about 50 milligram/kg body weight, about 100 milligram/kg body weight, about 750 milligrams/kg body weight or more per administration, and any range derivable therein. If the dose is administered weekly, the dose could be in the amount of 5 mg/kg body weight, or for example 350 mg of protein for a 70 kg subject.

XI. KITS

Provided are kits, such as therapeutic kits. For example, a kit may comprise one or more therapeutic composition as described herein and optionally instructions for their use. Kits may also comprise one or more devices for accomplishing administration of such compositions. For example, a subject kit may comprise a therapeutic composition and catheter for accomplishing direct intravenous injection of the composition into a target tissue. A kit may comprise pre-filled ampoules of a modified CGL enzyme, optionally formulated as a therapeutic composition, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a modified CGL enzyme that is effective for therapeutic or non-therapeutic applications, such as described above. The label on the container may indicate that the composition is used for a specific therapy or non-therapeutic application, and may also indicate directions for either in vivo or in vitro use, such as those described above. Kits will typically comprise the container described above and one or more other containers comprising materials desirable from a commercial and user standpoint, including buffers, diluents, filters, needles, syringes, and package inserts with instructions for use.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Treatment of a Mouse Model of Hyperhomocysteinemia with a Human Cystathionine-gamma-Lyase Variant Enzyme Classical homocystinuria is caused by a genetic defect in the cystathionine-β-synthase gene. Disruption of this metabolic pathway results in hyperhomocysteinemia, a condition where serum levels of total homocysteine (tHcy) are severely elevated. Hallmarks of homocystinuria include problems with the skeletal, ocular, vascular, and nervous systems. These symptoms are likely the result of homocysteine accumulation in serum as well as intracellularly.

The aim of this work is to develop a novel, enzymatic therapeutic capable of degrading excess serum homocysteine, providing a sink for intracellular homocysteine, and create a new treatment for homocystinuria. The human cystathionine-γ-lyase (CGL) enzyme has been engineered to degrade homocysteine and homocystine. Using random and rational mutagenesis, libraries of CGL variants were generated, and clones were identified through a genetic selection where degradation of homocysteine to α-ketobutyrate confers a growth advantage to an engineered strain of *E. coli*. The kinetics of the CGL variants were tested and are shown in Table 1.

Figure 2:
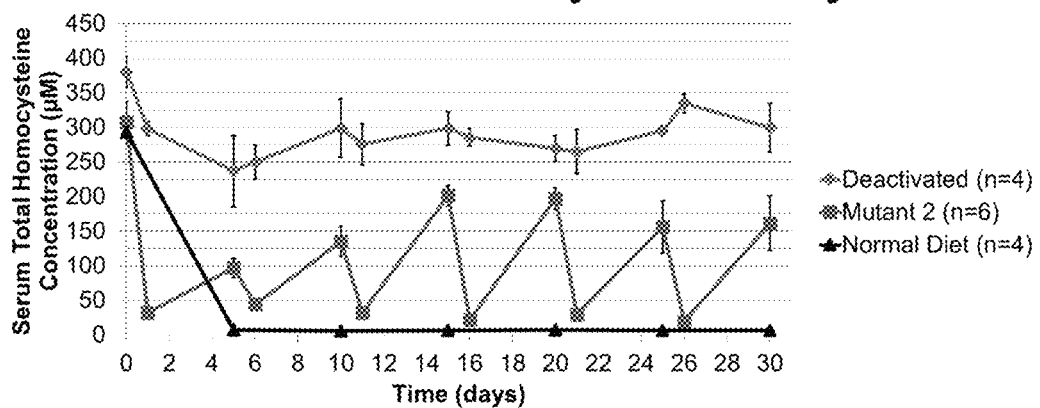
FIG. 2—Multi-dose Pharmacodynamics. Enzyme (hCGL-8mut-4; SEQ ID NO: 6) was dosed every 5 days at 50 mg/kg (i.p.). Serum was collected prior to every injection and 24 hours post injection.

Using a high methionine diet (2.5% w/w methionine as opposed to the 0.6% w/w methionine present in a normal rodent diet), hyperhomocysteinemia was induced in mice, creating a murine model to assess the efficacy of the developed enzymes. Administration of a single dose 50 mg/kg (i.p.) of the modified CGL in the high methionine diet mouse model significantly reduced tHcy from 380±13 μM to 44.7±4.8 μM within 24 hours (FIG. 1). Note that the level of tHcy in a normal mouse is about 4±0.5 μM. Dosing every 5 days for 30 days at 50 mg/kg (i.p.) resulted in a prolonged reduction in tHcy as shown in FIG. 2. Additionally the prolonged, frequent dosing did not result in weight loss or any other signs of toxicity. Administration of the enzyme successfully depleted tHcy in the diet-induced murine model without adverse effects. A high methionine diet is a normal rodent diet however with 4-fold more methionine content present.

Figure 3:
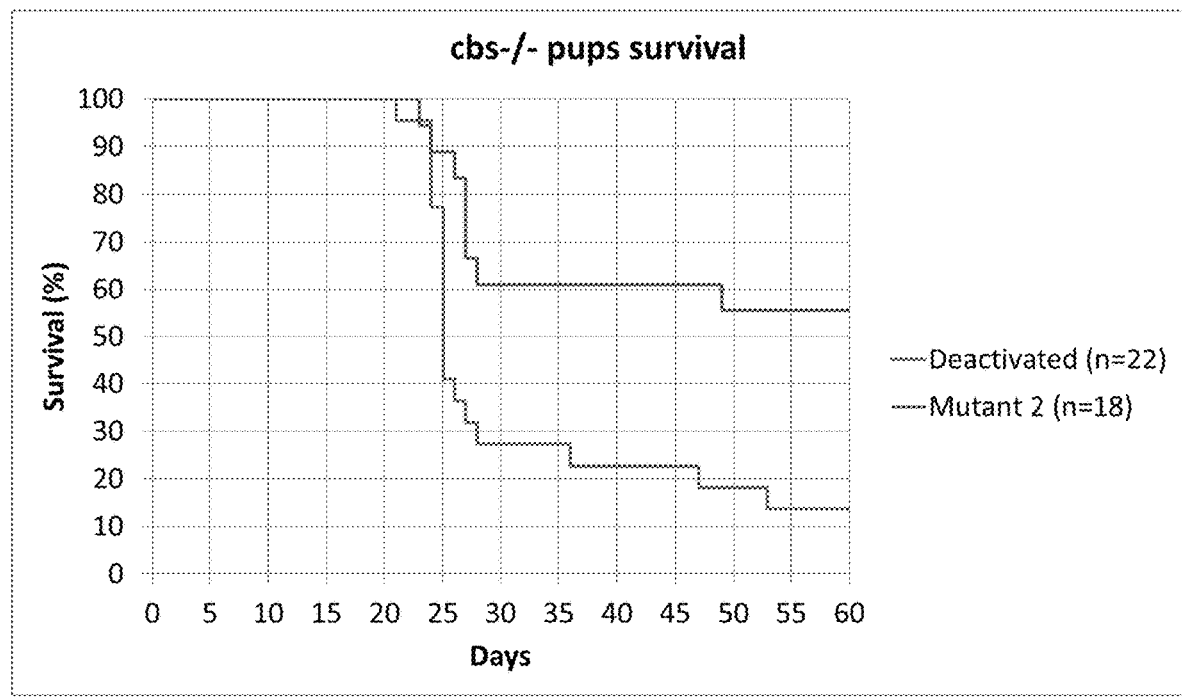
FIG. 3—In vivo Therapeutic Effect of Modified CGL. Enzyme (hCGL-8mut-4; SEQ ID NO: 6) was injected twice weekly starting at day 10 post birth. Top line represents modified CGL. Bottom line represents inactive enzyme.

In order to evaluate the therapeutic effect of the modified CGL (hCGL-8mut-4; Mutant 2; SEQ ID NO: 6), a cbs$^{-/-}$ murine strain, which results in neonatal lethality, was used. Modified CGL and inactive enzyme (20 mg/kg IP, twice weekly) were injected starting at day 10 and ended on day 50. A survival advantage was expected in the treated mice. Both the mothers' and the pups' diet included betaine, a dietary additive posited to improve survival for the disease. As shown in FIG. 3, treatment with modified CGL (Mutant 2) improved pup survival, suggesting that controlling Hcy levels is important for ameliorating disease.

Example 2—Design and Kinetic Characterization of Higher Specificity Homocysteine/Homocystine Degrading Variants The gene coding for the Mutant 2 enzyme (SEQ ID NO: 6) was used as a starting point to generate further variants with improvements in enzymatic activity or selectivity to homocysteine or homocystine. Active site residues hypothesized to coordinate substrate binding were selected for saturation mutagenesis and subsequent libraries were generated by overlap extension PCR (polymerase chain reaction). The final assembled PCR products were digested with NcoI and EcoRI and ligated into pET28a vector using T4 DNA ligase. The resulting ligations were transformed directly into *E. coli* (BL21) and plated on LB-kanamycin plates for subsequent screening (as described in U.S. Pat. No. 9,481,877, which is incorporated herein by reference in its entirety). Two times more colonies than the theoretical diversity of the libraries were screened. Clones displaying significant activity were isolated and sequenced to identify mutations conferring improved activity. Three variants were identified containing mutations at position R119 (Mutant 3: R119D, SEQ ID NO: 37; Mutant 4: R119H, SEQ ID NO: 38; Mutant 5: R119G, SEQ ID NO: 39) and were purified to greater than 95% homogeneity as assessed by SDS-PAGE and kinetically characterized for their ability to degrade Methionine, Cysteine, Cystine, Homocysteine, and Homocystine in a 100 mM PBS (phosphate-buffered saline) buffer at pH 7.3 and 37° C. (Table 1) (as described in U.S. Pat. No. 9,481,877, which is incorporated herein by reference in its entirety).

TABLE 1

Kinetics of CGL mutants $K_{cat}/k_M (s^{-1}mM^{-1})$

| | Methionine | Cysteine | Cystine | Homocysteine | Homocystine |
|---|---|---|---|---|---|
| Wild type | ND* | 0.2 | 0.85 | 0.2 | ND* |
| Mutant 1 | 0.75 | 2.7 | 2.6 | 8.0 | 7.6 |
| Mutant 2 | 5.3 | 8.5 | 2.1 | 12 | 21.6 |
| Mutant 3 | 1.1 | 3.6 | 2.3 | 11.9 | 18.8 |
| Mutant 4 | 2.7 | 4.7 | 1.9 | 11.7 | 17.7 |
| Mutant 5 | 1.7 | 5.4 | 2.1 | 13.1 | 20.7 |

*ND = no data

Figure 4:
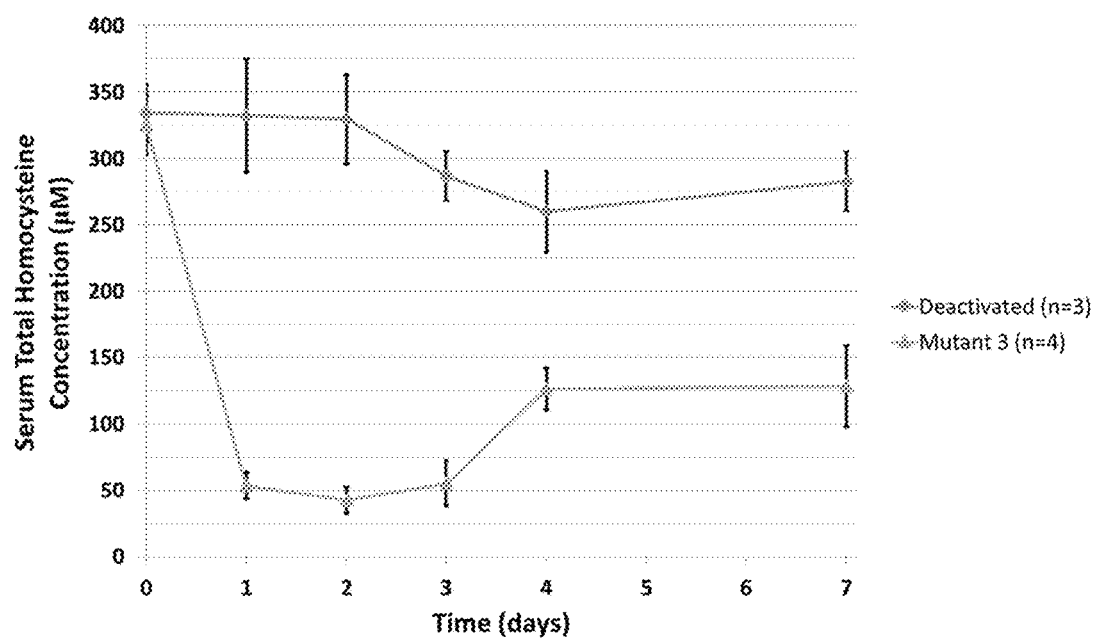
FIG. 4—Evaluation of Mutant 3 in vivo. Enzyme (Mutant 3; SEQ ID NO: 37) was dosed a single time at 50 mg/kg (i.p.). Serum was collected prior to the injection and every 24 hours post injection for a week. Top line represents deactivated enzyme. Bottom line represents Mutant 3 (SEQ ID NO: 37).

Example 3—Homocysteine Pharmacodynamics of Mutant 3 in Mice with a Diet-Induced Mouse Model of Hyperhomocysteinemia A high methionine diet (2.5% w/w as opposed to the normal 0.6% w/w as described in Example 1) was used to induce hyperhomocysteinemia in mice. Such mice were administered a single dose 50 mg/kg animal weight (i.p.) of either Mutant 3 (SEQ ID NO: 37) or deactivated enzyme. Mutant 3 in the high methionine diet mouse model resulted in a statistically significant reduction of tHcy from 335±37 μM to a nadir of 42±20 μM within 48 hours (FIG. 4).

Example 4—Treatment of Mouse Model of Hyperhomocysteinemia with Mutant 3

Figure 5:
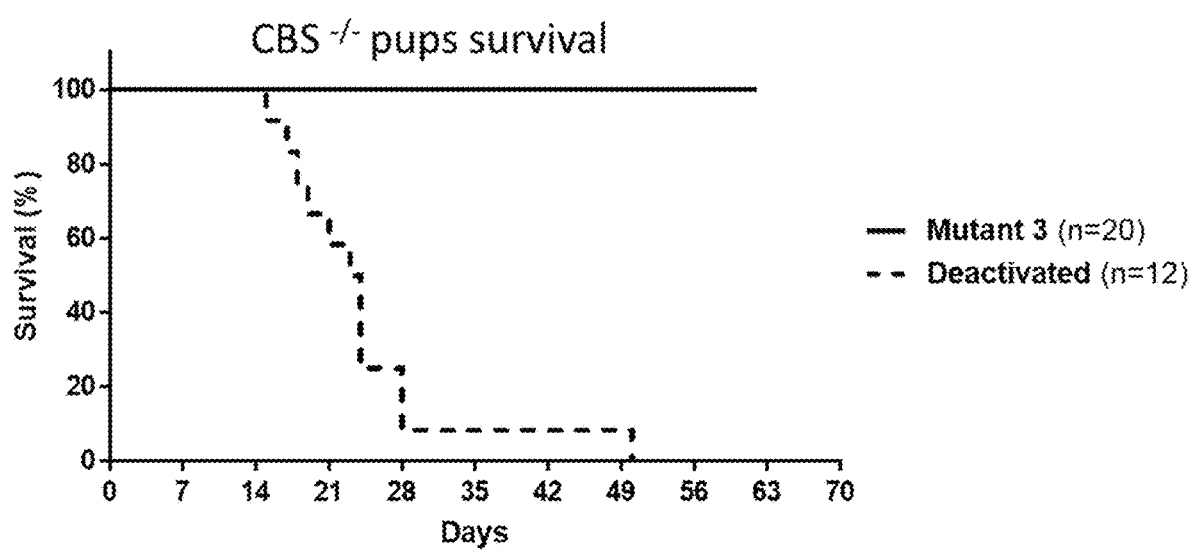
FIG. 5—In vivo Therapeutic Effect of Mutant 3. Enzyme (Mutant 3; SEQ ID NO: 37) was injected twice weekly starting at day 10 post birth.

In order to evaluate the therapeutic effect of the Mutant 3 (R119D; SEQ ID NO: 37), which displays the highest substrate selectivity for homocysteine/homocystine as compared to its methionine, cysteine, or cystine degrading activities, cbs$^{-/-}$ mouse pups were treated with either Mutant 3 or Mutant 3 enzyme that was heat deactivated by placing the sample in a boiling water bath for 10 minutes. The pups were injected starting at day 10 post birth at a dose of 25 mg/kg animal weight (i.p., twice weekly) until a final treatment on day 50. Both the mothers' and the pups' diet included betaine, a dietary additive posited to improve survival for the disease. As can be seen in FIG. 5, treatment with active Mutant 3 completely rescued cbs$^{-/-}$ mouse pups from neonatal lethality in contrast to animals administered an equivalent amount of deactivated enzyme.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,344
U.S. Pat. No. 5,830,880
U.S. Pat. No. 5,846,945
U.S. Pat. No. 5,889,155
U.S. Pat. No. 8,709,407
U.S. Pat. No. 9,481,877
U.S. Pat. Publn. 2009/0304666
U.S. Pat. Publn. 2011/0200576
Ashe et al., *Biochem. Biophys. Res. Commun.*, 57:417, 1974.
Austin-Ward and Villaseca, *Revista Medica de Chile*, 126 (7):838-845, 1998.
Ausubel et al., Current Protocols in Molecular Biology, Greene Publishing Associates and Wiley Interscience, N.Y., 1994.
Breillout et al., In: *Methionine dependency of malignant tumors: a possible approach for therapy*, Oxford University Press, 1628-1632, 1990.
Bukowski et al., *Clinical Cancer Res.*, 4(10):2337-2347, 1998.
Christodoulides et al., *Microbiology*, 144 (Pt 11):3027-3037, 1998.
Davidson et al., *J. Immunother.*, 21(5):389-398, 1998.
Esaki and Soda, *Methods Enzymol.*, 143: 459, 1987.
Gill and von Hippel, Calculation of protein extinction coefficients from amino acid sequence data. *Anal Biochem*, 182(2):319-326, 1989.
Halpern et al., *Proc. Natl. Acad. Sci.*, 71:1133-1136, 1974.
Hanibuchi et al., *Int. J. Cancer*, 78(4):480-485, 1998.
Harkki et al., *BioTechnology*, 7:596-603, 1989.
Hellstrand et al., *Acta Oncologica*, 37(4):347-353, 1998.
Hollander, *Front. Immun.*, 3:3, 2012.
Hoover & Lubkowski, DNAWorks: an automated method for designing oligonucleotides for PCR-based gene synthesis. Nucleic Acids Res., 30:e43-e, 2002.
Hopwood et al., In: *Genetic Manipulation of Streptomyces, A Laboratory Manual*, The John Innes Foundation, Norwich, Conn., 1985.
Hori et al., *Cancer Res.*, 56:2116-2122, 1996.
Hui and Hashimoto, *Infection Immun.*, 66(11):5329-5336, 1998.
Ito et al., *J. Biochem.*, 79:1263, 1976.
Kang et al. Homocysteinemia due to folate deficiency. *Metabolism*, 36:458-62, 1987.
Kreis and Goodenow, *Cancer Res.*, 38:2259-2262, 1978.
Kreis et al., *Cancer Res.*, 40:634-641, 1980.
Kreis, *Cancer Treatment Rpts.*, 63:1069, 1979.
Kruger et al. Cystathionine beta-synthase deficiency in Georgia (USA): correlation of clinical and biochemical phenotype with genotype. *Human Mutation*, 22:434-41, 2003.
Kudou et al., *J. Biochem.*, 141:535, 2007.
Lishko et al., *Anticancer Res.*, 13:1465-1468, 1993.
Lordanescu, *J. Bacteriol*, 12:597 601, 1975.
Lu et al., Cloning and nucleotide sequence of human liver cDNA encoding for cystathionine gamma-lyase. *Biochem. Biophys. Res. Comm.*, 189(2): 749-758, 1992.
Maniatis et al., Molecular Cloning, A Laboratory Manual, Cold Spring Harbor Press, Cold Spring Harbor, N.Y., 1988.
Mellor et al., *Gene*, 24:1-14, 1983.
Mudd et al., Homocystinuria: an enzymatic defect. *Science*, 143:1443-45, 1964.
Nakamura et al., *Anal. Biochem.*, 138:421-424, 1984.
Nygård et al., Major lifestyle determinants of plasma total homocysteine distribution: the Hordaland Homocysteine Study. The American Journal of Clinical Nutrition, 67:263-70, 1998.
Penttila et al., *Gene*, 61:155-164, 1987.
Qin et al., *Proc. Natl. Acad. Sci. USA*, 95(24):14411-14416, 1998.
Rao et al., Role of the Transsulfuration Pathway and of {gamma}-Cystathionase Activity in the Formation of Cysteine and Sulfate from Methionine in Rat Hepatocytes. *Journal of Nutrition*, 120(8):837, 1990.
Remington's Pharmaceutical Sciences, 18th Ed. Mack Printing Company, 1289-1329, 1990.
Sibakov et al., *Eur. J. Biochem.*, 145:567 572, 1984.
Sridhar et al., *Acta Crystall. Section D: Biolog, Crystall.*, 56:1665-1667, 2000.
Steegborn et al., Kinetics and inhibition of recombinant human cystathionine gamma-lyase. Toward the rational control of transsulfuration. *Journal of Biological Chemistry*, 274(18):12675, 1999.
Stone et al., De novo engineering of a human cystathionine-γ-lyase for systemic L-methionine depletion cancer therapy. *ACS Chemical Biology*, 7(11):1822-1829, 2012.
Takakura et al., Assay method for antitumor L-methionine-lyase: comprehensive kinetic analysis of the complex reaction with L-methionine. *Analytical Biochemistry*, 327 (2):233-240, 2004.
Tan et al., *Anticancer Res.*, 16:3937-3942, 1996a.
Tan et al., *Anticancer Res.*, 16:3931-3936, 1996b.
Tan et al., *Protein Express. Purif.*, 9:233-245, 1997a.
Tan et al., *Anticancer Res.*, 17:3857-3860, 1997b.
Walter et al. Strategies for the treatment of cystathionine beta-synthase deficiency: the experience of the Willink Biochemical Genetics Unit over the past 30 years. *European Journal of Pediatrics*, 157:S71-S76, 1998.
Ward, Proc, Embo-Alko Workshop on Molecular Biology of Filamentous Fungi, Helsinki, 119-128, 1989.
Wawrzynczak and Thorpe, In: *Immunoconjugates, Antibody Conuugates In Radioimaging And Therapy Of Cancer*, Vogel (Ed.), NY, Oxford University Press, 28, 1987.
Yang et al., In: *PEGylation confers greatly extended half-life and attenuated immunogenicity to recombinant methioninase in primates*, AACR, 6673-6678, 2004a.
Yang et al., In: *Pharmacokinetics, methionine depletion, and antigenicity of recombinant methioninase in primates*, AACR, 2131-2138, 2004b.
Yoshioka et al., *Cancer Res.*, 58:2583-2587, 1998.

What is claimed is:

1. A nucleic acid comprising a nucleotide sequence encoding a modified primate cystathionine-γ-lyase (CGL) enzyme comprising substitutions relative to a native human CGL amino acid sequence as shown in SEQ ID NO: 1, wherein the modified enzyme has both homocystinase and homocysteinase activity, wherein the modified enzyme comprises a sequence at least 95% identical to SEQ ID NO: 1, said substitutions comprising isoleucine at position 59, leucine at position 63, methionine at position 91, aspartic acid at position 119, arginine at position 268, glycine at position 311, valine at position 339, and serine at position 353.

2. The nucleic acid of claim 1, wherein the nucleic acid is codon optimized for expression in bacteria, fungus, insects, or mammals.

3. The nucleic acid of claim 2, wherein the bacteria are *E. coli*.

4. The nucleic acid of claim 3, wherein the nucleic acid comprises the nucleotide sequence of SEQ ID NO: 64.

5. An expression vector comprising the nucleic acid of claim 1.

6. A host cell comprising the nucleic acid of claim 1.

7. The host cell of claim 6, wherein the host cell is a bacterial cell, a fungal cell, an insect cell, or a mammalian cell.

8. The nucleic acid of claim 1, wherein the encoded enzyme is a modified human CGL enzyme.

9. The nucleic acid of claim 8, wherein the substitutions comprise E59I, S63L, L91M, R119D, K268R, T311G, E339V, and I353S relative to the native human CGL amino acid sequence as shown in SEQ ID NO: 1.

10. The nucleic acid of claim 8, wherein the modified human CGL enzyme has the amino acid sequence of SEQ ID NO: 37.

11. The nucleic acid of claim 1, wherein the encoded enzymes has a $k_{cat}/K_M$ for hydrolysis of homocysteine greater than the wild-type human CGL enzyme.

12. The nucleic acid of claim 1, wherein the encoded enzyme displays a $k_{cat}/K_M$ for hydrolysis of homocysteine of about 11.9 $s^{-1}mM^{-1}$ at pH 7.3 and 37° C.

13. The nucleic acid of claim 1, wherein the encoded enzyme displays a $k_{cat}/K_M$ for hydrolysis of homocysteine about 60-fold greater than wild-type human CGL.

14. The nucleic acid of claim 1, wherein the encoded enzyme displays a $k_{cat}/K_M$ for hydrolysis of homocystine of about 18.8 $s^{-1}mM^{-1}$ at pH 7.3 and 37° C.

15. The nucleic acid of claim 1, wherein the encoded enzyme displays a $k_{cat}/K_M$ for hydrolysis of homocysteine of about 11.9 $s^{-1}mM^{-1}$ at pH 7.3 and 37° C. and displays a $k_{cat}/K_M$ for hydrolysis of homocystine of about 18.8 $s^{-1}mM^{-1}$ at pH 7.3 and 37° C.

16. A pharmaceutical formulation comprising the nucleic acid of claim 1 in a pharmaceutically acceptable carrier.

* * * * *

SEQUENCE LISTING

<160> NUMBER OF SEQ ID NOS: 66

<210> SEQ ID NO 1
<211> LENGTH: 405
<212> TYPE: PRT
<213> ORGANISM: Homo sapiens

<400> SEQUENCE: 1

```
Met Gln Glu Lys Asp Ala Ser Ser Gln Gly Phe Leu Pro His Phe Gln
 1               5                  10                  15

His Phe Ala Thr Gln Ala Ile His Val Gly Gln Asp Pro Glu Gln Trp
             20                  25                  30

Thr Ser Arg Ala Val Val Pro Pro Ile Ser Leu Ser Thr Thr Phe Lys
         35                  40                  45

Gln Gly Ala Pro Gly Gln His Ser Gly Phe Glu Tyr Ser Arg Ser Gly
 50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Leu Ala Ala Thr Val Thr
             85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
            165                 170                 175

His Lys His Gly Asp Ile Ile Leu Val Val Asp Asn Thr Phe Met Ser
        180                 185                 190

Pro Tyr Phe Gln Arg Pro Leu Ala Leu Gly Ala Asp Ile Ser Met Tyr
    195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Lys His Phe Lys Asn
        260                 265                 270

Gly Met Ala Val Ala Gln Phe Leu Glu Ser Asn Pro Trp Val Glu Lys
    275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
```

```
                        405

<210> SEQ ID NO 2
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 2

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Asn Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
```

```
                355                 360                 365
Ile Ser Asp Thr Leu Ile Arg Leu Ser Val Gly Leu Glu Asp Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 3
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 3

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
        290                 295                 300

Arg Gln Cys Thr Gly Cys Gly Gly Met Val Thr Phe Tyr Ile Lys Gly
```

```
             305                 310                 315                 320
         Thr Leu Gln His Ala Glu Ile Phe Leu Lys Asn Leu Lys Leu Phe Thr
                         325                 330                 335

Leu Ala Val Ser Leu Gly Gly Phe Glu Ser Leu Ala Glu Leu Pro Ala
                         340                 345                 350

Ser Met Thr His Ala Ser Val Leu Lys Asn Asp Arg Asp Val Leu Gly
                         355                 360                 365

Ile Ser Asp Thr Leu Ile Arg Leu Ser Val Gly Leu Glu Asp Glu Glu
                         370                 375                 380

Asp Leu Leu Glu Asp Leu Asp Gln Ala Leu Lys Ala Ala His Pro Pro
         385                 390                 395                 400

Ser Gly Ser His Ser
                         405

<210> SEQ ID NO 4
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 4

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
```

```
            260                 265                 270
Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 5
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 5

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
```

```
                    210                 215                 220
Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                    245                 250                 255

Arg Gly Leu Lys Thr Leu His Val Arg Met Glu Arg His Phe Lys Asn
                    260                 265                 270

Gly Met Ala Val Ala Gln Phe Leu Glu Ser Asn Pro Trp Val Glu Lys
                275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                    325                 330                 335

Leu Ala Val Ser Leu Gly Gly Phe Glu Ser Leu Ala Glu Leu Pro Ala
                    340                 345                 350

Ser Met Thr His Ala Ser Val Leu Lys Asn Asp Arg Asp Val Leu Gly
                    355                 360                 365

Ile Ser Asp Thr Leu Ile Arg Leu Ser Val Gly Leu Glu Asp Glu Glu
                    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 6
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 6

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
                35                  40                  45

Gln Gly Ala Pro Gly Gln His Ser Gly Phe Ile Tyr Ser Arg Leu Gly
            50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                    100                 105                 110

Val Tyr Gly Gly Thr Asn Ala Tyr Phe Arg Gln Val Ala Ser Glu Phe
                115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
```

```
                165                 170                 175
His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Arg His Phe Lys Asn
        260                 265                 270

Gly Met Ala Val Ala Gln Phe Leu Glu Ser Asn Pro Trp Val Glu Lys
    275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Val Ser Leu Gly Gly Phe Glu Ser Leu Ala Glu Leu Pro Ala
        340                 345                 350

Ser Met Thr His Ala Ser Val Leu Lys Asn Asp Arg Asp Val Leu Gly
    355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 7
<211> LENGTH: 405
<212> TYPE: PRT
<213> ORGANISM: Pongo abelii

<400> SEQUENCE: 7

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Val Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Arg Tyr Phe Arg Gln Val Ala Ser Glu Phe
        115                 120                 125
```

| Gly | Leu | Lys | Ile | Ser | Phe | Val | Asp | Cys | Ser | Lys | Ile | Lys | Leu | Leu | Glu |
|---|---|---|---|---|---|---|---|---|---|---|---|---|---|---|---|
| 130 | | | | | 135 | | | | | 140 | | | | | |

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
            340                 345                 350

Val Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 8
<211> LENGTH: 405
<212> TYPE: PRT
<213> ORGANISM: Macaca fascicularis

<400> SEQUENCE: 8

Met Gln Glu Lys Asp Ala Ser Ser Gln Gly Phe Leu Pro His Phe Gln
1                   5                   10                  15

His Phe Ala Thr Gln Ala Ile His Val Gly Gln Glu Pro Glu Gln Trp
                20                  25                  30

Thr Ser Arg Ala Val Val Pro Leu Ile Ser Leu Ser Thr Thr Phe Lys
            35                  40                  45

Gln Ala Ala Pro Gly Gln His Ser Gly Phe Glu Tyr Ser Arg Ser Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

```
Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
            340                 345                 350

Ile Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 9
<211> LENGTH: 405
<212> TYPE: PRT
<213> ORGANISM: Pan troglodytes

<400> SEQUENCE: 9

Met Gln Glu Lys Asp Ala Ser Ser Gly Phe Leu Pro His Phe Gln
1                   5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
```

-continued

```
               50                  55                  60
Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Leu Ala Ala Thr Val Thr
                     85                  90                  95

Ile Thr His Leu Leu Lys Ala Gly Asp Gln Ile Ile Cys Met Asp Asp
                    100                 105                 110

Val Tyr Gly Gly Thr Asn Arg Tyr Phe Arg Gln Val Ala Ser Glu Phe
                    115                 120                 125

Gly Leu Lys Ile Ser Phe Val Asp Cys Ser Lys Ile Lys Leu Leu Glu
                    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                    165                 170                 175

His Lys His Gly Asp Ile Ile Leu Val Val Asp Asn Thr Phe Met Ser
                    180                 185                 190

Pro Tyr Phe Gln Arg Pro Leu Ala Leu Gly Ala Asp Ile Cys Met Tyr
                    195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                    245                 250                 255

Arg Gly Leu Lys Thr Leu His Val Arg Met Glu Lys His Phe Lys Asn
                    260                 265                 270

Gly Met Ala Val Ala Gln Phe Leu Glu Ser Asn Pro Trp Val Glu Lys
                    275                 280                 285

Val Ile Tyr Pro Gly Leu Pro Ser His Pro Gln His Glu Leu Val Lys
                    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                    325                 330                 335

Leu Ala Glu Ser Leu Gly Gly Phe Glu Ser Leu Ala Glu Leu Pro Ala
                    340                 345                 350

Ile Met Thr His Ala Ser Val Leu Lys Asn Asp Arg Asp Val Leu Gly
                    355                 360                 365

Ile Ser Asp Thr Leu Ile Arg Leu Ser Val Gly Leu Glu Asp Glu Glu
                    370                 375                 380

Asp Leu Leu Glu Asp Leu Asp Gln Ala Leu Lys Ala Ala His Pro Pro
385                 390                 395                 400

Ser Gly Ser His Ser
                405
```

<210> SEQ ID NO 10
<211> LENGTH: 405
<212> TYPE: PRT
<213> ORGANISM: Pan paniscus

<400> SEQUENCE: 10

```
Met Gln Glu Lys Asp Ala Ser Ser Gln Gly Phe Leu Pro His Phe Gln
 1               5                  10                  15
```

His Phe Ala Thr Gln Ala Ile His Val Gly Gln Asp Pro Glu Gln Trp
                20                  25                  30

Thr Ser Lys Ala Leu Val Pro Pro Ile Ser Leu Ser Thr Thr Phe Lys
         35                  40                  45

Gln Gly Ala Pro Gly Gln His Ser Gly Phe Glu Tyr Ser Arg Ser Gly
     50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                 85                  90                  95

Ile Thr His Leu Leu Lys Ala Gly Asp Gln Ile Ile Cys Met Asp Asp
                100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 11
<211> LENGTH: 405
<212> TYPE: PRT

<213> ORGANISM: Artificial Sequence
<220> FEATURE:
<223> OTHER INFORMATION: Synthetic polypeptide

<400> SEQUENCE: 11

```
Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
```

```
            385                 390                 395                 400

Ser Gly Ser His Ser
                    405

<210> SEQ ID NO 12
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 12

Met Gln Glu Lys Glu Ala Ser Ser Gln Gly Phe Leu Pro His Phe Gln
1               5                  10                  15

His Phe Ala Thr Gln Ala Ile His Val Gly Gln Glu Pro Glu Gln Trp
                20                  25                  30

Thr Ser Arg Ala Val Val Pro Pro Ile Ser Pro Ser Val Thr Phe Lys
            35                  40                  45

Gln Gly Ala Pro Gly Gln His Ser Gly Phe Ile Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
```

```
                    340                 345                 350
Ser Met Thr His Ala Ser Val Leu Lys Lys Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 13
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 13

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
```

```
                290                 295                 300
Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Leu Lys Lys Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 14
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 14

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Pro Ile Ser Pro Ser Val Thr Phe Lys
            35                  40                  45

Gln Gly Ala Pro Gly Gln His Ser Gly Phe Ile Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Ala Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
        210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
```

```
                    245                 250                 255
Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
        290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Leu Lys Lys Asp Arg Asp Val Leu Gly
                355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 15
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 15

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
```

```
                195                 200                 205
Ser Ala Thr Lys Tyr Met Asn Gly His Ser Asp Val Val Met Gly Leu
210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Gly Val Glu Lys
                275                 280                 285

Val Ile Tyr Pro Gly Leu Pro Ser His Pro Gln His Glu Leu Ala Lys
                290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Pro Lys Asn Asp Arg Asp Val Leu Gly
                355                 360                 365

Ile Ser Asp Thr Leu Ile Arg Leu Ser Val Gly Leu Glu Asp Glu Lys
                370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 16
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 16

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Leu Ile Ser Leu Ser Thr Thr Phe Lys
                35                  40                  45

Gln Ala Ala Pro Gly Gln His Ser Gly Phe Ile Tyr Ser Arg Leu Gly
                50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
                115                 120                 125

Gly Leu Lys Ile Ser Phe Val Asp Cys Ser Lys Ile Lys Leu Leu Glu
                130                 135                 140

Ala Ala Ile Thr Pro Glu Thr Lys Leu Val Trp Ile Glu Thr Pro Thr
```

```
            145                 150                 155                 160
Asn Pro Val Leu Lys Met Ile Asp Ile Glu Ala Cys Ala His Ile Val
                    165                 170                 175

His Lys Arg Gly Asp Ile Ile Leu Val Val Asp Asn Thr Phe Met Ser
                    180                 185                 190

Pro Tyr Phe Gln Arg Pro Leu Ala Leu Gly Ala Asp Ile Cys Met Cys
                    195                 200                 205

Ser Ala Thr Lys Tyr Met Asn Gly His Ser Asp Val Val Met Gly Leu
                    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                    245                 250                 255

Arg Gly Leu Lys Thr Leu His Val Arg Met Glu Arg His Phe Lys Asn
                    260                 265                 270

Gly Met Ala Val Ala Gln Phe Leu Glu Ser Asn Pro Gly Val Glu Lys
                    275                 280                 285

Val Ile Tyr Pro Gly Leu Pro Ser His Pro Gln His Glu Leu Ala Lys
                    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                    325                 330                 335

Leu Ala Val Ser Leu Gly Gly Phe Glu Ser Leu Val Glu Leu Pro Ala
                    340                 345                 350

Ser Met Thr His Ala Ser Val Pro Lys Asn Asp Arg Asp Val Leu Gly
                    355                 360                 365

Ile Ser Asp Thr Leu Ile Arg Leu Ser Val Gly Leu Glu Asp Glu Lys
                    370                 375                 380

Asp Leu Leu Glu Asp Leu Asp Gln Ala Leu Lys Ala Ala His Pro Pro
385                 390                 395                 400

Ser Gly Ser His Asn
                    405

<210> SEQ ID NO 17
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 17

Met Gln Glu Lys Asp Ala Ser Ser Gln Gly Phe Leu Pro His Phe Gln
1                   5                   10                  15

His Phe Ala Thr Gln Ala Ile His Val Gly Gln Glu Pro Glu Gln Trp
                    20                  25                  30

Thr Ser Arg Ala Val Val Pro Leu Ile Ser Leu Ser Thr Thr Phe Lys
                    35                  40                  45

Gln Ala Ala Pro Gly Gln His Ser Gly Phe Asn Tyr Ser Arg Leu Gly
                    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                    85                  90                  95

Ile Thr His Leu Leu Lys Ala Gly Asp Gln Ile Ile Cys Met Asp Asp
```

```
            100                 105                 110
Val Tyr Gly Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys His Ile Val
                165                 170                 175

His Lys Arg Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
        210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Gly Val Glu Lys
            275                 280                 285

Val Ile Tyr Pro Gly Leu Pro Ser His Pro Gln His Glu Leu Ala Lys
        290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Pro Lys Asn Asp Arg Asp Val Leu Gly
            355                 360                 365

Ile Ser Asp Thr Leu Ile Arg Leu Ser Val Gly Leu Glu Asp Glu Lys
        370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 18
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 18

Met Gln Glu Lys Asp Ala Ser Ser Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Leu Ile Ser Leu Ser Thr Thr Phe Lys
            35                  40                  45

Gln Ala Ala Pro Gly Gln His Ser Gly Phe Ile Tyr Ser Arg Leu Gly
```

50                  55                  60
Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Met Ala Ala Thr Val Thr
                 85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 19
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 19

Met Gln Glu Lys Asp Ala Ser Ser Gln Gly Phe Leu Pro His Phe Gln

-continued

```
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
            50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
            85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
            165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Met Gly Leu
            210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 20
```

<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 20

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 21
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 21

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

```
Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 22
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 22

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285
```

-continued

```
Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 23
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 23

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Lys Ala Leu Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Ile Gly Leu
        210                 215                 220

Val Ser Val Asn Cys Glu Ser Leu His Asn Arg Leu Arg Phe Leu Gln
225                 230                 235                 240
```

```
Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
                275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 24
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 24

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Lys Ala Leu Val Pro Pro Ile Ser Leu Ser Thr Thr Phe Lys
                35                  40                  45

Gln Gly Ala Pro Gly Gln His Ser Gly Phe Ile Tyr Ser Arg Leu Gly
            50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
                180                 185                 190
```

```
Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Ile Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
                275                 280                 285

Val Ile Tyr Pro Gly Leu Pro Ser His Pro Gln His Glu Leu Val Lys
                290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 25
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 25

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140
```

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 26
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 26

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 27
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 27

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Asn Tyr Ser Arg Ser Gly
            50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Leu Ala Ala Thr Val Thr
                 85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 28
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 28

-continued

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
50                      55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
        290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
            405
```

```
<210> SEQ ID NO 29
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 29

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365
```

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 30
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 30

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
        290                 295                 300

Arg Gln Cys Thr Gly Cys Gly Gly Met Val Thr Phe Tyr Ile Lys Gly
305                 310                 315                 320

-continued

```
Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 31
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 31

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270
```

```
Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 32
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 32

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Ser Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220
```

```
Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Glu
                325                 330                 335

Leu Ala Val Ser Leu Gly Gly Phe Glu Ser Leu Ala Glu Leu Pro Ala
                340                 345                 350

Ile Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 33
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 33

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Leu Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175
```

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
            210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Glu
            325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 34
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 34

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Ile Tyr Ser Arg Leu Gly
            50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
            85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
            115                 120                 125

```
Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
                195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Glu
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 35
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 35

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80
```

Ala Lys Tyr Cys Leu Ala Phe Ala Ser Gly Met Ala Thr Val Thr
            85                  90                  95

Ile Thr His Leu Leu Lys Ala Gly Asp Gln Ile Ile Cys Met Asp Asp
        100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Ser Met Tyr
                195                 200                 205

Ser Ala Thr Lys Tyr Met Asn Gly His Ser Asp Val Val Met Gly Leu
                210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
                275                 280                 285

Val Ile Tyr Pro Gly Leu Pro Ser His Pro Gln His Glu Leu Val Lys
                290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Glu
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 36
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 36

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Pro Pro Ile Ser Leu Ser Thr Phe Lys
         35                  40                  45

Gln Gly Ala Pro Gly Gln His Ser Gly Phe Ile Tyr Ser Arg Leu Gly
 50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Met Ala Ala Thr Val Thr
                 85                  90                  95

Ile Thr His Leu Leu Lys Ala Gly Asp Gln Ile Ile Cys Met Asp Asp
                100                 105                 110

Val Tyr Gly Gly Thr Asn Ala Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Glu
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 37
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 37

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Pro Ile Ser Leu Ser Thr Thr Phe Lys
            35                  40                  45

Gln Gly Ala Pro Gly Gln His Ser Gly Phe Ile Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Asp Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser

<210> SEQ ID NO 38
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 38

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
```

```
                355                 360                 365
Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 39
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 39

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Gly Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
```

```
                305                 310                 315                 320
Thr Leu Gln His Ala Glu Ile Phe Leu Lys Asn Leu Lys Leu Phe Thr
                325                 330                 335
Leu Ala Val Ser Leu Gly Gly Phe Glu Ser Leu Ala Glu Leu Pro Ala
                340                 345                 350
Ser Met Thr His Ala Ser Val Leu Lys Asn Asp Arg Asp Val Leu Gly
                355                 360                 365
Ile Ser Asp Thr Leu Ile Arg Leu Ser Val Gly Leu Glu Asp Glu Glu
                370                 375                 380
Asp Leu Leu Glu Asp Leu Asp Gln Ala Leu Lys Ala Ala His Pro Pro
385                 390                 395                 400
Ser Gly Ser His Ser
                405

<210> SEQ ID NO 40
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 40

Met Gln Glu Lys Glu Ala Ser Ser Gln Gly Phe Leu Pro His Phe Gln
1               5                   10                  15
His Phe Ala Thr Gln Ala Ile His Val Gly Gln Glu Pro Glu Gln Trp
                20                  25                  30
Thr Ser Arg Ala Val Val Pro Pro Ile Ser Pro Ser Val Thr Phe Lys
                35                  40                  45
Gln Gly Ala Pro Gly Gln His Ser Gly Phe Ile Tyr Ser Arg Leu Gly
                50                  55                  60
Asn Pro Thr Arg Asn Cys Leu Glu Lys Ala Val Ala Ala Leu Asp Gly
65                  70                  75                  80
Ala Lys Tyr Cys Leu Ala Phe Ala Ser Gly Met Ala Ala Thr Val Thr
                85                  90                  95
Ile Thr His Leu Leu Lys Ala Gly Asp Gln Ile Ile Cys Met Asp Asp
                100                 105                 110
Val Tyr Ala Gly Thr Asn Asp Tyr Phe Arg Gln Val Ala Ser Glu Phe
                115                 120                 125
Gly Leu Lys Ile Ser Phe Val Asp Cys Ser Lys Ile Lys Leu Leu Glu
                130                 135                 140
Ala Ala Ile Thr Pro Glu Thr Lys Leu Val Trp Ile Glu Thr Pro Thr
145                 150                 155                 160
Asn Pro Thr Gln Lys Met Thr Asp Ile Glu Ala Cys Ala His Ile Val
                165                 170                 175
His Lys His Gly Asp Ile Ile Leu Val Val Asp Asn Thr Phe Met Ser
                180                 185                 190
Pro Tyr Phe Gln Arg Pro Leu Ala Leu Gly Ala Asp Ile Cys Met Cys
                195                 200                 205
Ser Ala Thr Lys Tyr Met Asn Gly His Ser Asp Val Val Met Gly Leu
                210                 215                 220
Val Ser Val Asn Cys Glu Ser Leu Tyr Asn Arg Leu Arg Phe Leu Gln
225                 230                 235                 240
Asn Ser Leu Gly Ala Val Pro Ser Pro Ile Asp Cys Tyr Leu Cys Asn
                245                 250                 255
Arg Gly Leu Lys Thr Leu Gln Val Arg Met Glu Arg His Phe Lys Asn
```

```
            260                 265                 270
Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Leu Lys Lys Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 41
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 41

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Pro Ile Ser Pro Ser Val Thr Phe Lys
            35                  40                  45

Gln Gly Ala Pro Gly Gln His Ser Gly Phe Ile Tyr Ser Arg Leu Gly
50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Ala Gly Thr Asn His Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
```

```
        210                 215                 220
Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Leu Lys Lys Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 42
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 42

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Pro Ile Ser Pro Ser Val Thr Phe Lys
            35                  40                  45

Gln Gly Ala Pro Gly Gln His Ser Gly Phe Ile Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Ala Gly Thr Asn Gly Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
```

```
                    165                 170                 175
His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 43
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 43

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Asp Tyr Phe Arg Gln Val Ala Ser Glu Phe
```

```
            115                 120                 125
Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 44
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 44

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Leu Ile Ser Leu Ser Thr Thr Phe Lys
            35                  40                  45

Gln Ala Ala Pro Gly Gln His Ser Gly Phe Ile Tyr Ser Arg Leu Gly
        50                  55                  60

Asn Pro Thr Arg Asn Cys Leu Glu Lys Ala Val Ala Ala Leu Asp Gly
```

```
             65                  70                  75                  80
Ala Lys Tyr Cys Leu Ala Phe Ala Ser Gly Met Ala Ala Thr Val Thr
                 85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
            275                 280                 285

Val Ile Tyr Pro Gly Leu Pro Ser His Pro Gln His Glu Leu Ala Lys
            290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
            355                 360                 365

Ile Ser Asp Thr Leu Ile Arg Leu Ser Val Gly Leu Glu Asp Glu Lys
            370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 45
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 45

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
```

```
            20                  25                  30
Thr Ser Arg Ala Val Val Pro Leu Ile Ser Leu Ser Thr Phe Lys
        35                  40                  45
Gln Ala Ala Pro Gly Gln His Ser Gly Phe Ile Tyr Ser Arg Leu Gly
    50                  55                  60
Asn Pro Thr Arg Asn Cys Leu Glu Lys Ala Val Ala Ala Leu Asp Gly
65                  70                  75                  80
Ala Lys Tyr Cys Leu Ala Phe Ala Ser Gly Met Ala Ala Thr Val Thr
                85                  90                  95
Ile Thr His Leu Leu Lys Ala Gly Asp Gln Ile Ile Cys Met Asp Asp
                100                 105                 110
Val Tyr Gly Gly Thr Asn Gly Tyr Phe Arg Gln Val Ala Ser Glu Phe
            115                 120                 125
Gly Leu Lys Ile Ser Phe Val Asp Cys Ser Lys Ile Lys Leu Leu Glu
        130                 135                 140
Ala Ala Ile Thr Pro Glu Thr Lys Leu Val Trp Ile Glu Thr Pro Thr
145                 150                 155                 160
Asn Pro Val Leu Lys Met Ile Asp Ile Glu Ala Cys Ala His Ile Val
                165                 170                 175
His Lys Arg Gly Asp Ile Ile Leu Val Val Asp Asn Thr Phe Met Ser
                180                 185                 190
Pro Tyr Phe Gln Arg Pro Leu Ala Leu Gly Ala Asp Ile Cys Met Cys
            195                 200                 205
Ser Ala Thr Lys Tyr Met Asn Gly His Ser Asp Val Val Met Gly Leu
        210                 215                 220
Val Ser Val Asn Cys Glu Arg Leu His Asn Arg Leu Arg Phe Leu Gln
225                 230                 235                 240
Asn Ser Leu Gly Ala Val Pro Ser Pro Leu Asp Cys Tyr Leu Cys Asn
                245                 250                 255
Arg Gly Leu Lys Thr Leu His Val Arg Met Glu Arg His Phe Lys Asn
                260                 265                 270
Gly Met Ala Val Ala Gln Phe Leu Glu Ser Asn Pro Gly Val Glu Lys
            275                 280                 285
Val Ile Tyr Pro Gly Leu Pro Ser His Pro Gln His Glu Leu Ala Lys
        290                 295                 300
Arg Gln Cys Thr Gly Cys Gly Gly Met Ile Thr Phe Tyr Ile Lys Gly
305                 310                 315                 320
Thr Leu Gln His Ala Glu Ile Phe Leu Lys Asn Leu Lys Leu Phe Thr
                325                 330                 335
Leu Ala Val Ser Leu Gly Gly Phe Glu Ser Leu Val Glu Leu Pro Ala
                340                 345                 350
Ser Met Thr His Ala Ser Val Pro Lys Asn Asp Arg Asp Val Leu Gly
            355                 360                 365
Ile Ser Asp Thr Leu Ile Arg Leu Ser Val Gly Leu Glu Asp Glu Lys
        370                 375                 380
Asp Leu Leu Glu Asp Leu Asp Gln Ala Leu Lys Ala Ala His Pro Pro
385                 390                 395                 400
Ser Gly Ser His Asn
                405

<210> SEQ ID NO 46
<211> LENGTH: 405
<212> TYPE: PRT
<213> ORGANISM: Artificial Sequence
```

<220> FEATURE:
<223> OTHER INFORMATION: Synthetic polypeptide

<400> SEQUENCE: 46

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Asp Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 47
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 47

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

```
Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 48
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 48

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300
```

```
Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 49
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 49

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Asp Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255
```

Arg Gly Leu Lys Thr Leu His Val Arg Met Glu Arg His Phe Lys Asn
              260                 265                 270

Gly Met Ala Val Ala Gln Phe Leu Glu Ser Asn Pro Trp Val Glu Lys
              275                 280                 285

Val Ile Tyr Pro Gly Leu Pro Ser His Pro Gln His Glu Leu Val Lys
              290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
              325                 330                 335

Leu Ala Val Ser Leu Gly Gly Phe Glu Ser Leu Ala Glu Leu Pro Ala
              340                 345                 350

Ser Met Thr His Ala Ser Val Leu Lys Asn Asp Arg Asp Val Leu Gly
              355                 360                 365

Ile Ser Asp Thr Leu Ile Arg Leu Ser Val Gly Leu Glu Asp Glu Glu
              370                 375                 380

Asp Leu Leu Glu Asp Leu Asp Gln Ala Leu Lys Ala Ala His Pro Pro
385                 390                 395                 400

Ser Gly Ser His Ser
              405

<210> SEQ ID NO 50
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 50

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
              20                  25                  30

Thr Ser Lys Ala Leu Val Pro Pro Ile Ser Leu Ser Thr Thr Phe Lys
              35                  40                  45

Gln Gly Ala Pro Gly Gln His Ser Gly Phe Ile Tyr Ser Arg Leu Gly
         50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
              85                  90                  95

Ile Thr His Leu Leu Lys Ala Gly Asp Gln Ile Ile Cys Met Asp Asp
              100                 105                 110

Val Tyr Gly Gly Thr Asn His Tyr Phe Arg Gln Val Ala Ser Glu Phe
              115                 120                 125

Gly Leu Lys Ile Ser Phe Val Asp Cys Ser Lys Ile Lys Leu Leu Glu
         130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
              165                 170                 175

His Lys His Gly Asp Ile Ile Leu Val Val Asp Asn Thr Phe Met Ser
              180                 185                 190

Pro Tyr Phe Gln Arg Pro Leu Ala Leu Gly Ala Asp Ile Cys Met Tyr
              195                 200                 205

Ser Ala Thr Lys Tyr Met Asn Gly His Ser Asp Val Val Ile Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
                260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
        290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
                340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 51
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 51

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Gly Tyr Phe Arg Gln Val Ala Ser Glu Phe
            115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

```
Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 52
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 52

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110
```

Val Tyr Ala Gly Thr Asn Asp Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 53
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 53

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Leu Asp Gly
 65                  70                  75                  80

Ala Lys Tyr Cys Leu Ala Phe Ala Ser Gly Met Ala Ala Thr Val Thr
                 85                  90                  95

Ile Thr His Leu Leu Lys Ala Gly Asp Gln Ile Ile Cys Met Asp Asp
            100                 105                 110

Val Tyr Ala Gly Thr Asn His Tyr Phe Arg Gln Val Ala Ser Glu Phe
                115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Leu Lys Lys Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 54
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 54

Met Gln Glu Lys Glu Ala Ser Ser Gln Gly Phe Leu Pro His Phe Gln
 1               5                  10                  15

His Phe Ala Thr Gln Ala Ile His Val Gly Gln Glu Pro Glu Gln Trp
             20                  25                  30

Thr Ser Arg Ala Val Pro Pro Ile Ser Pro Ser Val Thr Phe Lys
         35                  40                  45

Gln Gly Ala Pro Gly Gln His Ser Gly Phe Asn Tyr Ser Arg Leu Gly
 50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Met Ala Ala Thr Val Thr
             85                  90                  95

Ile Thr His Leu Leu Lys Ala Gly Asp Gln Ile Ile Cys Met Asp Asp
             100                 105                 110

Val Tyr Ala Gly Thr Asn Gly Tyr Phe Arg Gln Val Ala Ser Glu Phe
         115                 120                 125

Gly Leu Lys Ile Ser Phe Val Asp Cys Ser Lys Ile Lys Leu Leu Glu
 130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
             165                 170                 175

His Lys His Gly Asp Ile Ile Leu Val Val Asp Asn Thr Phe Met Ser
         180                 185                 190

Pro Tyr Phe Gln Arg Pro Leu Ala Leu Gly Ala Asp Ile Cys Met Cys
 195                 200                 205

Ser Ala Thr Lys Tyr Met Asn Gly His Ser Asp Val Val Met Gly Leu
             210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
             245                 250                 255

Arg Gly Leu Lys Thr Leu Gln Val Arg Met Glu Arg His Phe Lys Asn
         260                 265                 270

Gly Met Ala Val Ala Gln Phe Leu Glu Ser Asn Pro Trp Val Glu Lys
 275                 280                 285

Val Ile Tyr Pro Gly Leu Pro Ser His Pro Gln His Glu Leu Val Lys
 290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
             325                 330                 335

Leu Ala Val Ser Leu Gly Gly Phe Glu Ser Leu Val Glu Leu Pro Ala
         340                 345                 350

Ser Met Thr His Ala Ser Val Leu Lys Lys Asp Arg Asp Val Leu Gly
             355                 360                 365

Ile Ser Asp Thr Leu Ile Arg Leu Ser Val Gly Leu Glu Asp Glu Glu
         370                 375                 380

Asp Leu Leu Glu Asp Leu Asp Gln Ala Leu Lys Ala Ala His Pro Pro
385                 390                 395                 400

Ser Gly Ser His Ser
             405

<210> SEQ ID NO 55
<211> LENGTH: 405

```
<212> TYPE: PRT
<213> ORGANISM: Artificial Sequence
<220> FEATURE:
<223> OTHER INFORMATION: Synthetic polypeptide

<400> SEQUENCE: 55

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Asp Tyr Phe Arg Gln Val Ala Ser Glu Phe
            115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380
```

```
Asp Leu Leu Glu Asp Leu Asp Gln Ala Leu Lys Ala Ala His Pro Pro
385                 390                 395                 400

Ser Gly Ser His Asn
            405

<210> SEQ ID NO 56
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 56

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335
```

```
Leu Ala Val Ser Leu Gly Gly Phe Glu Ser Leu Val Glu Leu Pro Ala
                340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 57
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 57

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285
```

```
Val Ile Tyr Pro Gly Leu Pro Ser His Pro Gln His Glu Leu Ala Lys
290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
                340                 345                 350

Ser Met Thr His Ala Ser Val Pro Lys Asn Asp Arg Asp Val Leu Gly
                355                 360                 365

Ile Ser Asp Thr Leu Ile Arg Leu Ser Val Gly Leu Glu Asp Glu Lys
370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 58
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 58

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Leu Val Pro Pro Ile Ser Leu Ser Thr Thr Phe Lys
            35                  40                  45

Gln Gly Ala Pro Gly Gln His Ser Gly Phe Asn Tyr Ser Arg Leu Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Asp Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240
```

```
Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 59
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 59

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190
```

```
Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
    275                 280                 285

Val Ile Tyr Pro Gly Leu Pro Ser His Pro Gln His Glu Leu Val Lys
290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
    355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 60
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 60

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Gly Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140
```

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 61
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 61

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Asp Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 62
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 62

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
 50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Met Ala Ala Thr Val Thr
                 85                  90                  95

Ile Thr His Leu Leu Lys Ala Gly Asp Gln Ile Ile Cys Met Asp Asp
            100                 105                 110

Val Tyr Gly Gly Thr Asn His Tyr Phe Arg Gln Val Ala Ser Glu Phe
            115                 120                 125

Gly Leu Lys Ile Ser Phe Val Asp Cys Ser Lys Ile Lys Leu Leu Glu
130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Ile Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 63
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 63

-continued

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Val Ser Leu Gly Gly Phe Glu Ser Leu Ala Glu Leu Pro Ala
        340                 345                 350

Ser Met Thr His Ala Ser Val Leu Lys Asn Asp Arg Asp Val Leu Gly
    355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
            405
```

<210> SEQ ID NO 64
<211> LENGTH: 1245
<212> TYPE: DNA
<213> ORGANISM: Artificial Sequence
<220> FEATURE:
<223> OTHER INFORMATION: Synthetic polynucleotide

<400> SEQUENCE: 64

| | |
|---|---|
| atgggaggcc atcaccacca tcatcatggc gggcaggaaa aggatgcgag ctcccagggc | 60 |
| tttcttccgc atttccagca ttttgcgacg caggcgatac acgtgggcca agacccggaa | 120 |
| cagtggacgt cgcgtgcggt tgtaccgccg attagcctga gcacgacctt aaacaaggt | 180 |
| gcgccgggcc agcatagcgg ttttatttat agccgtctgg gcaatcccac acggaattgc | 240 |
| ctggagaagg cggtggcggc tctggacggc gcgaagtatt gccttgcgtt tgcgagcgga | 300 |
| atggcggcca ccgtgaccat tacccacctg cttaaggctg gggaccagat tatttgcatg | 360 |
| gatgatgtgt atggtgggac caatgattat ttccgtcagg tggcgagcga gttcggcctg | 420 |
| aagatatcct ttgtcgactg ctcgaagatc aagctgttag aggcagcgat tacgccggaa | 480 |
| acaaaacttg tgtggataga aaccccgacg aacccgaccc agaaagtgat tgacattgaa | 540 |
| ggctgcgccc acattgtgca taaacacggc gatatcatcc tggtcgtgga taataccttc | 600 |
| atgagcccgt acttccagcg tccgctggcg cttggcgccg acattagcat gtattcggcg | 660 |
| accaagtata tgaacggcca tagcgacgtt gtcatgggcc tggtgagcgt gaattgcgag | 720 |
| agcctgcata atcgtctgcg ttttctgcaa aattcgcttg agcggtgcc gagcccgatc | 780 |
| gattgctatc tgtgcaatcg tgggctgaag actctgcatg tgcggatgga gagacatttt | 840 |
| aagaatggca tggctgtggc gcagtttctg gaaagcaatc cgtgggtgga aaaagttatc | 900 |
| tacccgggac tgcccagcca cccgcagcat gaactggtca acgtcagtg cacaggttgc | 960 |
| ggcggcatgg tgaccttcta tatcaagggc accctgcaac acgccgaaat ctttctgaaa | 1020 |
| aacctgaaac tgtttaccct ggcagtgagc ttgggcggct ttgaaagcct tgctgaactg | 1080 |
| ccggccagta tgactcatgc ctccgtgttg aaaaatgatc gtgatgttct gggcataagc | 1140 |
| gataccctga ttcgcctgtc cgtaggactg gaagatgaag aagatctgct ggaggatctg | 1200 |
| gatcaggcgc tgaaagcggc ccatccccca tcgggaagcc acagt | 1245 |

<210> SEQ ID NO 65
<211> LENGTH: 1245
<212> TYPE: DNA
<213> ORGANISM: Artificial Sequence
<220> FEATURE:
<223> OTHER INFORMATION: Synthetic polynucleotide

<400> SEQUENCE: 65

| | |
|---|---|
| atgggaggcc atcaccacca tcatcatggc gggcaggaaa aggatgcgag ctcccagggc | 60 |
| tttcttccgc atttccagca ttttgcgacg caggcgatac acgtgggcca agacccggaa | 120 |
| cagtggacgt cgcgtgcggt tgtaccgccg attagcctga gcacgacctt aaacaaggt | 180 |
| gcgccgggcc agcatagcgg ttttatttat agccgtctgg gcaatcccac acggaattgc | 240 |
| ctggagaagg cggtggcggc tctggacggc gcgaagtatt gccttgcgtt tgcgagcgga | 300 |
| atggcggcca ccgtgaccat tacccacctg cttaaggctg gggaccagat tatttgcatg | 360 |
| gatgatgtgt atggtgggac caatcattat ttccgtcagg tggcgagcga gttcggcctg | 420 |
| aagatatcct ttgtcgactg ctcgaagatc aagctgttag aggcagcgat tacgccggaa | 480 |
| acaaaacttg tgtggataga aaccccgacg aacccgaccc agaaagtgat tgacattgaa | 540 |

| | |
|---|---|
| ggctgcgccc acattgtgca taaacacggc gatatcatcc tggtcgtgga taataccttc | 600 |
| atgagcccgt acttccagcg tccgctggcg cttggcgccg acattagcat gtattcggcg | 660 |
| accaagtata tgaacggcca tagcgacgtt gtcatgggcc tggtgagcgt gaattgcgag | 720 |
| agcctgcata atcgtctgcg ttttctgcaa aattcgcttg agcggtgcc gagcccgatc | 780 |
| gattgctatc tgtgcaatcg tgggctgaag actctgcatg tgcggatgga gagacatttt | 840 |
| aagaatggca tggctgtggc gcagtttctg gaaagcaatc cgtgggtgga aaaagttatc | 900 |
| tacccgggac tgcccagcca cccgcagcat gaactggtca acgtcagtg cacaggttgc | 960 |
| ggcggcatgg tgaccttcta tatcaagggc accctgcaac acgccgaaat ctttctgaaa | 1020 |
| aacctgaaac tgtttaccct ggcagtgagc ttggcggct tgaaaagcct tgctgaactg | 1080 |
| ccggccagta tgactcatgc ctccgtgttg aaaaatgatc gtgatgttct gggcataagc | 1140 |
| gatacctga ttcgcctgtc cgtaggactg gaagatgaag aagatctgct ggaggatctg | 1200 |
| gatcaggcgc tgaaagcggc ccatccccca tcgggaagcc acagt | 1245 |

<210> SEQ ID NO 66
<211> LENGTH: 1245
<212> TYPE: DNA
<213> ORGANISM: Artificial Sequence
<220> FEATURE:
<223> OTHER INFORMATION: Synthetic polynucleotide

<400> SEQUENCE: 66

| | |
|---|---|
| atgggaggcc atcaccacca tcatcatggc gggcaggaaa aggatgcgag ctcccagggc | 60 |
| tttcttccgc atttccagca ttttgcgacg caggcgatac acgtgggcca agacccggaa | 120 |
| cagtggacgt cgcgtgcggt tgtaccgccg attagcctga gcacgacctt taaacaaggt | 180 |
| gcgccgggcc agcatagcgg ttttatttat agccgtctgg gcaatcccac acggaattgc | 240 |
| ctggagaagg cggtggcggc tctggacggc gcgaagtatt gccttgcgtt tgcgagcgga | 300 |
| atggcggcca ccgtgaccat tacccacctg cttaaggctg gggaccagat tatttgcatg | 360 |
| gatgatgtgt atggtgggac caatggttat ttccgtcagg tggcgagcga gttcggcctg | 420 |
| aagatatcct ttgtcgactg ctcgaagatc aagctgttag aggcagcgat tacgccggaa | 480 |
| acaaaacttg tgtggataga acccgacg aacccgaccc agaaagtgat tgacattgaa | 540 |
| ggctgcgccc acattgtgca taaacacggc gatatcatcc tggtcgtgga taataccttc | 600 |
| atgagcccgt acttccagcg tccgctggcg cttggcgccg acattagcat gtattcggcg | 660 |
| accaagtata tgaacggcca tagcgacgtt gtcatgggcc tggtgagcgt gaattgcgag | 720 |
| agcctgcata atcgtctgcg ttttctgcaa aattcgcttg agcggtgcc gagcccgatc | 780 |
| gattgctatc tgtgcaatcg tgggctgaag actctgcatg tgcggatgga gagacatttt | 840 |
| aagaatggca tggctgtggc gcagtttctg gaaagcaatc cgtgggtgga aaaagttatc | 900 |
| tacccgggac tgcccagcca cccgcagcat gaactggtca acgtcagtg cacaggttgc | 960 |
| ggcggcatgg tgaccttcta tatcaagggc accctgcaac acgccgaaat ctttctgaaa | 1020 |
| aacctgaaac tgtttaccct ggcagtgagc ttggcggct tgaaaagcct tgctgaactg | 1080 |
| ccggccagta tgactcatgc ctccgtgttg aaaaatgatc gtgatgttct gggcataagc | 1140 |
| gatacctga ttcgcctgtc cgtaggactg gaagatgaag aagatctgct ggaggatctg | 1200 |
| gatcaggcgc tgaaagcggc ccatccccca tcgggaagcc acagt | 1245 |